US011213252B2

(12) United States Patent
Cross et al.

(10) Patent No.: US 11,213,252 B2
(45) Date of Patent: Jan. 4, 2022

(54) DEVICES AND SENSING METHODS FOR MEASURING TEMPERATURE FROM AN EAR

(71) Applicant: Starkey Hearing Technologies, Eden Prairie, MN (US)

(72) Inventors: Peggi S. Cross, Tucson, AZ (US); Kyle Olson, St. Louis Park, MN (US); Sourav Bhunia, Shoreview, MN (US); Kaysar Rahim, Mechanicville, NY (US); Dave Tourtelotte, Eden Prairie, MN (US)

(73) Assignee: Starkey Laboratories, Inc., Eden Prairie, MN (US)

( * ) Notice: Subject to any disclaimer, the term of this patent is extended or adjusted under 35 U.S.C. 154(b) by 511 days.

(21) Appl. No.: 16/160,695

(22) Filed: Oct. 15, 2018

(65) Prior Publication Data

US 2019/0117155 A1    Apr. 25, 2019

Related U.S. Application Data

(60) Provisional application No. 62/575,038, filed on Oct. 20, 2017.

(51) Int. Cl.
*A61B 5/00* (2006.01)
*A61B 5/01* (2006.01)
(Continued)

(52) U.S. Cl.
CPC .............. *A61B 5/6817* (2013.01); *A61B 5/01* (2013.01); *G01K 7/427* (2013.01); *G01K 13/20* (2021.01);
(Continued)

(58) Field of Classification Search
CPC ... A61B 5/742; A61B 2562/0276; A61B 5/72; A61B 5/6803; A61B 2562/0271;
(Continued)

(56) References Cited

U.S. PATENT DOCUMENTS 5,673,692 A   10/1997   Schulze et al.
6,631,287 B2  10/2003   Newman et al.
(Continued)

FOREIGN PATENT DOCUMENTS

DE   202010016226 U1 *  2/2011  ........... A61B 5/6817
DE   202010016226        3/2011
(Continued)

OTHER PUBLICATIONS

Nakada Hirofumi et al: "Development of a method for estimating oesophageal temperature by multi-locational temperature measurement inside the external auditory canal", International Journal of Biometeorology, vol. 81, No. 9,. Apr. 8, 2017 (Apr. 8, 2017), pp. 1545-1554 (Year: 2017).*

(Continued)

*Primary Examiner* — Christine H Matthews
*Assistant Examiner* — Joshua Daryl D Lannu
(74) *Attorney, Agent, or Firm* — Mueting Raasch Group

(57) ABSTRACT

An electronic device comprises an enclosure configured for insertion into the ear canal and comprising a distal end configured to extend at least beyond a first bend of the ear canal. A distal temperature sensor is situated at a location of the enclosure that faces a tragus-side of the ear canal between the first and second bends when the enclosure is fully inserted into the ear canal. A proximal temperature sensor is situated on the enclosure at a location spaced apart from a surface of the ear canal and proximal of the distal temperature sensor in an outer ear direction when the enclosure is fully inserted into the ear canal. A processor, (Continued)

coupled to the distal and proximal temperature sensors and to memory, is configured to calculate an absolute core body temperature using a heat balance equation stored in the memory and the first and second temperature signals.

23 Claims, 24 Drawing Sheets

(51) Int. Cl.
    *H04R 25/00*     (2006.01)
    *G01K 7/42*     (2006.01)
    *G01K 13/20*     (2021.01)

(52) U.S. Cl.
    CPC ........... *H04R 25/30* (2013.01); *H04R 25/652* (2013.01); *A61B 5/6803* (2013.01); *A61B 5/72* (2013.01); *A61B 5/742* (2013.01); *A61B 2562/0271* (2013.01); *A61B 2562/0276* (2013.01)

(58) Field of Classification Search
    CPC ........ A61B 5/01; A61B 5/6817; G01K 13/20; G01K 7/427; H04R 25/652; H04R 25/30
    See application file for complete search history.

(56) References Cited

U.S. PATENT DOCUMENTS

| | | | |
|---|---|---|---|
| 6,821,249 | B2 | 11/2004 | Casscells, III et al. |
| 7,306,565 | B2 | 12/2007 | Fraden et al. |
| 7,410,290 | B2 | 8/2008 | Tanaka et al. |
| 7,665,892 | B2 | 2/2010 | Hsieh |
| 8,467,562 | B2 | 6/2013 | Wada |
| 8,511,892 | B2 | 8/2013 | Koch |
| 8,652,040 | B2 | 2/2014 | LeBoeuf et al. |
| 10,779,090 | B2 | 9/2020 | Larsen et al. |
| 2005/0177029 | A1 | 8/2005 | Shen |
| 2005/0209516 | A1* | 9/2005 | Fraden ............... A61B 5/02055 600/323 |
| 2008/0072153 | A1 | 3/2008 | Yang |
| 2008/0146890 | A1 | 6/2008 | Leboeuf et al. |
| 2009/0131761 | A1 | 5/2009 | Moroney, III et al. |
| 2017/0127193 | A1 | 5/2017 | Husung |
| 2020/0296524 | A1 | 9/2020 | Troelsen et al. |

FOREIGN PATENT DOCUMENTS

| | | |
|---|---|---|
| EP | 3576434 | 12/2019 |
| JP | 2010236897 | 10/2010 |
| JP | 2010236897 A * | 10/2010 |

OTHER PUBLICATIONS

Amiya et al, "Diurnal body temperature rise is reduced in diabetes with autonomic neuropathy," Clinical Autonomic Research, vol. 24, (2), pp. 95-97, 2014.
Benzinger et al., "Temperature—Its Measurement Control in Science and Industry," New York: Reinhold, vol. 3, (3), p. 111, 1963.
Calonder et al, "Temperature Measurement in Patients Undergoing Colorectal Surgery and Gynecology Surgery: A Comparison of Esophageal Core, Temporal Artery, and Oral Methods," Journal of PeriAnesthesia Nursing, vol. 25, (2), pp. 71-78, 2010.
Cooper et al., "Temperature in the external auditory meatus as an index of central temperature changes," Journal of Applied Physiology, vol. 19, pp. 1032, 1964.
Duffy et al., "Age-related change in the relationship between circadian period, circadian phase, and diurnal preference in humans," Neuroscience Letters, vol. 318, (3), pp. 117-120, 2002.
Erickson et al. "Accuracy of infrared ear thermometry and other temperature methods in adults," American Journal of Critical Care: An Official Publication, American Association of Critical-Care Nurses, vol. 3, (1), pp. 40, 1994.
Gibson et al, "Power relative to body mass best predicts change in core temperature during exercise-heat stress," Journal of Strength and Conditioning Research, vol. 31, (2), pp. 403, 2016; 2017.
Greenleaf et al., "External auditory canal temperature as an estimate of core temperature," 1972.
Gubin et al. "Disrupted circadian rhythms of body temperature, heart rate and fasting blood glucose in prediabetes and type 2 diabetes mellitus," Chronobiol Int. Jul. 31, 2017:1-13. doi: 10.1080/07420528.2017.1347670.
Imafuku, "Body temperature rhythm and control of the time of the best physical condition by performing physical labor," Chronobiology International, vol. 33, (4), pp. 431-434, 2016.
Jesdanun, "Sales for wearables is strong, but users are abandoning them quickly after", Business Insider 2015 internet access Oct. 10, 2017 http://www.businessinsider.com/sales-for-wearables-is-strong-but-users-are-abandoning-them-quickly-after-2015-7.
Kimberger et al, "The accuracy of a disposable noninvasive core thermometer," Canadian Journal of Anesthesia/Journal Canadien d'Anesthésie, vol. 60, (12), pp. 1190-1196, 2013.
McIntosh et al., "Wind Noise Measurements and Characterization Around Small Microphone Ports," Audio Engineering Society Convention 139, 2015.
Micic et al, "The endogenous circadian temperature period length (tau) in delayed sleep phase disorder compared to good sleepers," Journal of Sleep Research, vol. 22, (6), pp. 617-624, 2013.
Pranskunas et al, "Effects of whole body heat stress on sublingual microcirculation in healthy humans," European Journal of Applied Physiology, vol. 115, (1), pp. 157-165, 2015.
Sato et al, "Reexamination of tympanic membrane temperature as a core temperature," Journal of Applied Physiology, vol. 80, (4), pp. 1233-1239, 1996.
Weinert et al., "The circadian rhythm of core temperature: Effects of physical activity and aging," Physiology & Behavior, vol. 90, (2), pp. 246-256, 2007.
Williams et al., "A Device for Obtaining a Continuous Record of Body Temperature from the External Auditory Canal," Science, vol. 108, (2795), pp. 90-91, 1948.
Wright, "Early evolution of the thermometer and application to clinical medicine," Journal of Thermal Biology, vol. 56, pp. 18-30, 2016.
International Search Report and Written Opinion dated Jan. 17, 2019 from PCT Application No. PCT/US2018/056279, 16 pages.
Nakada et al., "Development of a method for estimating oesophageal temperature by multi-locational temperature measurement inside the external auditory canal", Int J. Biometeorol., vol. 61, No. 1, 2017, pp. 1545-1554.
Baker et al., "Sleep and 24-hour body temperatures: a comparison in young men, naturally cycling women and women taking hormonal contraceptives," The Journal of Physiology, vol. 530, (3), pp. 565-574, 2001.
Bland et al., "Statistical methods for assessing agreement between two methods of clinical measurement," International Journal of Nursing Studies, vol. 47, (8), pp. 931-936, 2010.
Gagnon et al., "Aural canal, esophageal, and rectal temperatures during exertional heat stress and the subsequent recovery period," Journal of Athletic Training, vol. 45, (2), pp. 157-163, 2010.
Ganio et al., "Validity and reliability of devices that assess body temperature during indoor exercise in the heat," Journal of Athletic Training, vol. 44, (2), pp. 124-135, 2009.
Gunga et al., "A non-invasive device to continuously determine heat strain in humans," Journal of Thermal Biology, vol. 33, (5), pp. 297-307, 2008.
Gunga et al., "The Double Sensor—A non-invasive device to continuously monitor core temperature in humans on earth and in space," Respiratory Physiology & Neurobiology, vol. 169, pp. S63-S68, 2009.
Hagni et al., "Wearable Devices in Medical Internet of Things: Scientific Research and Commercially Available Devices," Healthcare Informatics Research, vol. 23, (1), pp. 4-15, 2017.
Hitchcock et al., "Metabolic and thermoregulatory responses to simulated football practice in the heat," Journal of Strength and Conditioning Research, vol. 21, (3), pp. 710-717, 2007.

(56) References Cited

OTHER PUBLICATIONS

Ishii et al., "Usefulness of a simple device to measure aural canal temperature," The Annals of Physiological Anthropology = Seiri Jinruigaku Kenkyūkai Kaishi, vol. 12, (3), pp. 189, 1993.

Kenny et al., "Hyperthermia and cardiovascular strain during an extreme heat exposure in young versus older adults," Temperature, vol. 4, (1), pp. 79-10, 2017; 2016.

Kimberger et al., "Accuracy and precision of a novel non-invasive core thermometer," British Journal of Anaesthesia, vol. 103, (2), pp. 226-231, 2009.

Korstanje et al., "Continuous Glucose Monitoring in female NOD Mice Reveals Daily Rhythms and a Negative Correlation with Body Temperature," Endocrinology Jun. 19, 2017. doi: 10.1210/en.2017-00266. Unpublished.

Low et al., "Sympathetic nerve activity and whole body heat stress in humans," Journal of Applied Physiology, vol. 111, (5), pp. 1329-1334, 2011.

Muir et al., "Prediction of rectal temperature from ear canal temperature," Ergonomics, vol. 44, (11), pp. 962-972, 2001.

Passias, "Effects of hypoglycemia on thermoregulation", 1993 PhD thesis Simon Fraser University, Canada. Internet Access: summit.sfu.ca/system/files/iritems1/5760/b15282831.pdf.

Pompei et al., "Arterial Thermometry Via Heat Balance at the Ear," Physicians Reference Handbook of Temperature, 1996.

Pompei et al., "Noninvasive temporal artery thermometry: Physics, physiology, and clinical accuracy," in 2004, . DOI: 10.1117/12.544841.

Sejling et al., "Infrared thermographic assessment of changes in skin temperature during hypoglycaemia in patients with type 1 diabetes," Diabetologia, vol. 58, (8), pp. 1898-1906, 2015.

Wingo et al., "Skin blood flow and local temperature independently modify sweat rate during passive heat stress in humans," Journal of Applied Physiology, vol. 109, (5), pp. 1301-1306, 2010.

\* cited by examiner

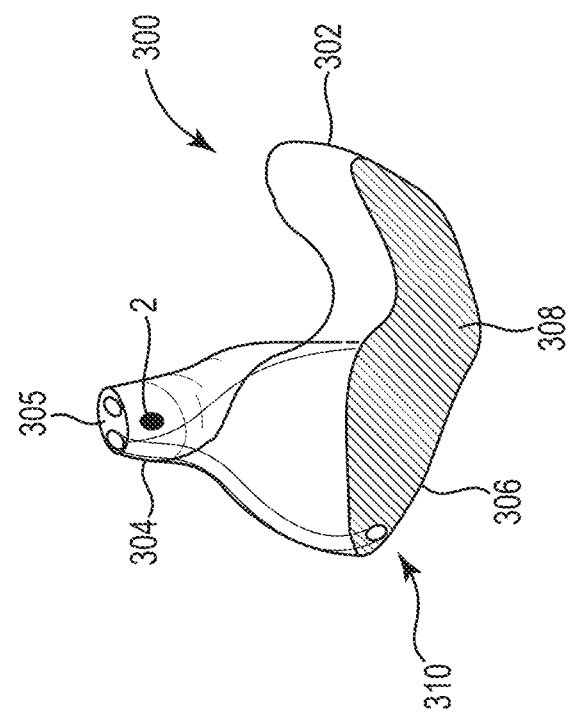
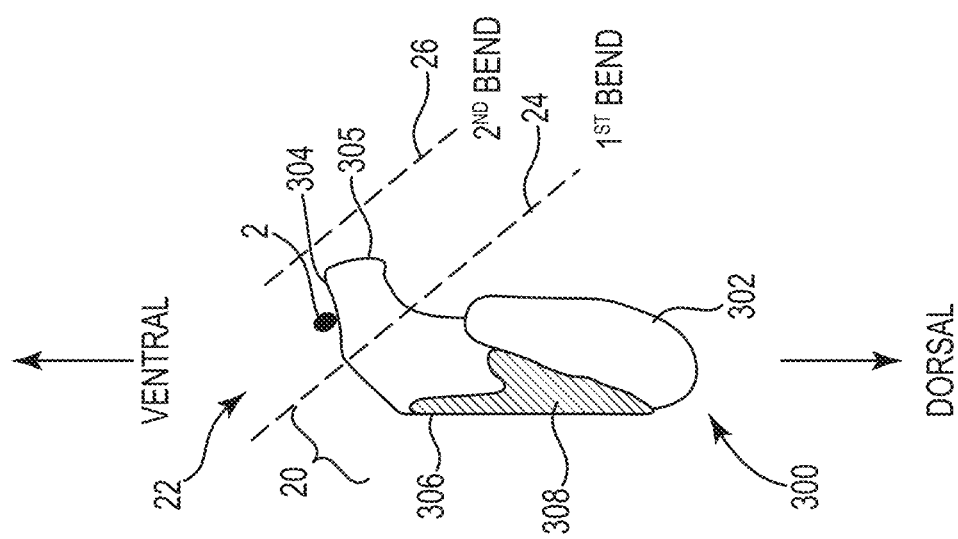
Figure 3B
Figure 3A

DEVICES AND SENSING METHODS FOR MEASURING TEMPERATURE FROM AN EAR

RELATED PATENT DOCUMENTS

This application claims the benefit of Provisional Patent Application Ser. No. 62/575,038 filed on Oct. 20, 2017, to which priority is claimed pursuant to 35 U.S.C. § 119(e), and which is incorporated herein by reference in its entirety.

TECHNICAL FIELD

This application relates generally to devices and sensing methods for measuring temperature from an ear, such devices including ear-worn electronic devices, hearing devices, hearing aids, personal amplification devices, and other hearables, and hand-held temperature probes.

BACKGROUND

Measuring body temperature and changes in body temperature is key to assessing various health conditions. One area of the body that can be used to capture accurate temperature measurements is the ear. Measuring temperature from the ear is typically done from the tympanic membrane using a handheld IR sensor. The primary challenge with acquiring tympanic membrane temperature measurements using a handheld IR sensor is obtaining a direct field of view from the measurement sensor to the tympanic membrane through a narrow and often angular ear canal.

SUMMARY

Various embodiments are directed to an electronic device configured to measure temperature from within an ear canal of an ear comprising a first bend and a second bend. The device comprises an enclosure configured for insertion into the ear canal and comprising a distal end configured to extend at least beyond the first bend. A distal temperature sensor is situated at a location of the enclosure that faces a tragus-side of the ear canal distal to the first bend and proximal to the second bend when the enclosure is fully inserted into the ear canal. The distal temperature sensor is configured to sense one or both of conductive heat and convective heat and to produce a first temperature signal. A proximal temperature sensor is situated on the enclosure at a location spaced apart from a surface of the ear canal and proximal of the distal temperature sensor in an outer ear direction when the enclosure is fully inserted into the ear canal. The proximal temperature sensor is configured to sense one or both of conductive heat and convective heat and to produce a second temperature signal. A memory is configured to store a pre-established heat balance equation. A processor is coupled to the distal and proximal temperature sensors and to the memory. The processor is configured to calculate an absolute core body temperature using the heat balance equation and the first and second temperature signals.

Various embodiments are directed to a method implemented by an electronic device configured for insertion into an ear canal of an ear, the ear canal comprising a first bend, a second bend, and a tragus-side. The method comprises measuring a first temperature indicative of one or both of conductive heat and convective heat at the tragus-side of the ear canal between the first and second bends. The method comprises measuring a second temperature indicative of one or both of conductive heat and convective heat at a location spaced apart from a surface of the ear canal and proximal of an ear canal location where the first temperature is measured in an outer ear direction. The method also comprises storing, in a memory of the device, a pre-established heat balance equation. The method further comprises calculating, using a processor of the device, an absolute core body temperature using the heat balance equation and the first and second temperatures.

Various embodiments are directed to an ear-worn electronic device configured to be worn in an ear of a wearer and to measure temperature from within an ear canal of the ear comprising a first bend and a second bend. The device comprises an enclosure configured for insertion into the ear canal and comprising a distal end configured to extend at least beyond the first bend. A distal temperature sensor is situated at a location of the enclosure that faces a tragus-side of the ear canal distal to the first bend and proximal to the second bend when the enclosure is fully inserted into the ear canal. The distal temperature sensor is configured to sense one or both of conductive heat and convective heat and to produce a first temperature signal. A proximal temperature sensor is situated on the enclosure at a location in the ear that is spaced apart from a surface of the ear canal and proximal of the distal temperature sensor in an outer ear direction when the enclosure is fully inserted into the ear canal. The proximal temperature sensor is configured to sense one or both of conductive heat and convective heat and to produce a second temperature signal. A memory is configured to store a pre-established heat balance equation. A processor is coupled to the distal and proximal temperature sensors and to the memory. The processor is configured to calculate an absolute core body temperature using the heat balance equation and the first and second temperature signals.

The above summary is not intended to describe each disclosed embodiment or every implementation of the present disclosure. The figures and the detailed description below more particularly exemplify illustrative embodiments.

BRIEF DESCRIPTION OF THE DRAWINGS

Throughout the specification reference is made to the appended drawings wherein:

FIGS. 3A and 3B show a representative ear-worn device positioned relative to a preferred location of the ear canal from which temperature measurements can be obtained in accordance with various embodiments;

The figures are not necessarily to scale. Like numbers used in the figures refer to like components. However, it will be understood that the use of a number to refer to a component in a given figure is not intended to limit the component in another figure labeled with the same number.

DETAILED DESCRIPTION

Figure 1:
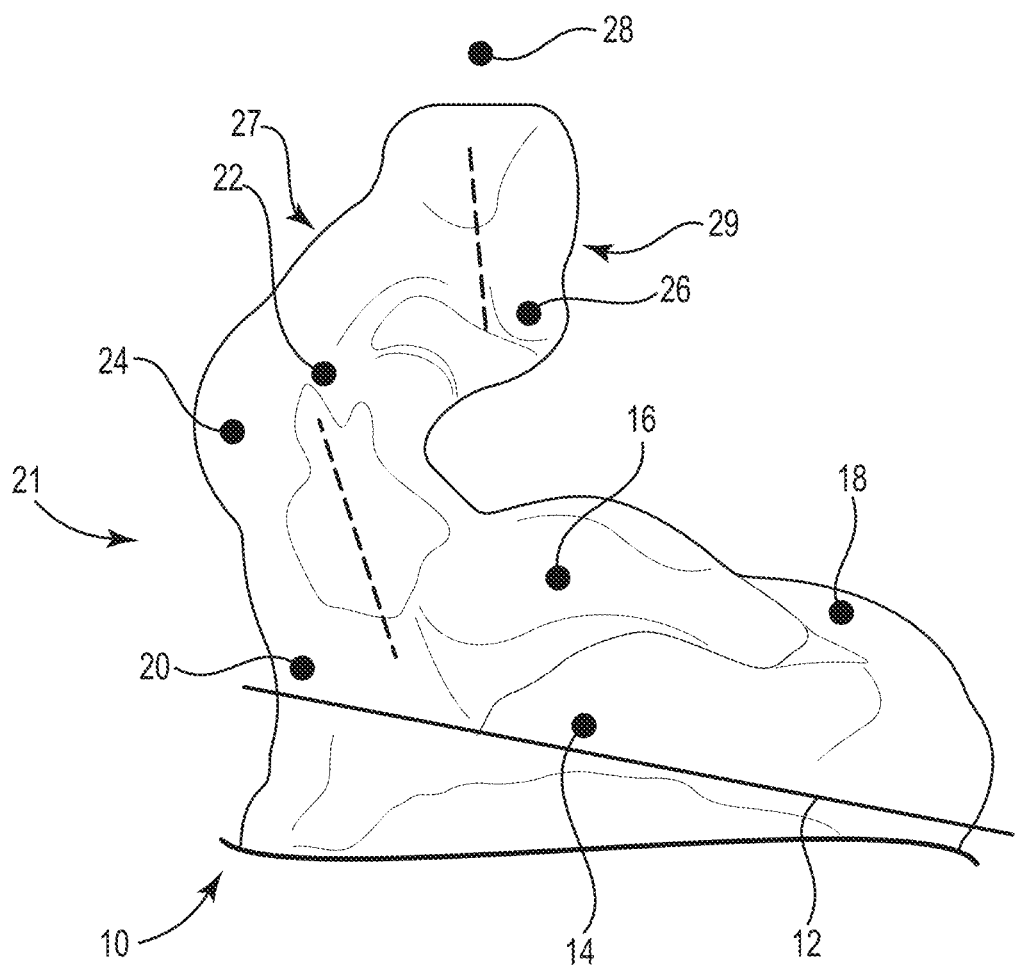
FIG. 1 is an illustration of a person's ear including various anatomical features.

Valuable health information can be derived from measurement of human body temperature. Absolute core body temperature has been used as a key vital sign to detect fever and infection. Continuous measurement of absolute core body temperature provides valuable information about a person's health status. For example, the change in temperature can be monitored as a health indicator, to prevent heat stress during endurance activity or exposure to extreme temperatures, or detect decreases in body temperature due to hypoglycemia or diabetes In addition, changes in the circadian rhythm of temperature occur in aging, diabetes, and persons with altered sleep cycles. By measuring these changes, it may be possible to obtain valuable information about transitions from health to disease states leading to the discovery of preventive methods and better disease management protocols.

A significant problem for continuous biometric measurements is that people often lose interest in wearable devices within months. Hearing aid users, however, typically wear their devices during all waking hours making them ideal for the integration of health monitoring sensors. The ear also provides a mechanically stable location for sensors, but is limited by the need for small device sizes and low power consumption requirements. Attempts to obtain accurate measurements from the ear have had limited success in the past.

Early attempts were made to measure temperature directly from the tympanic membrane using contact thermocouples. Multiple researchers then attempted to avoid the danger and discomfort of taking measurements directly from the tympanic membrane by placing thermistors further out in the ear canal. One such researcher concluded that there is a considerable temperature gradient down the wall of the external auditory meatus so that absolute temperature levels are probably not of value. Researchers at the NASA Ames Research Center in Mountain View, Calif. used temperature sensors placed 8 to 10 mm from the tympanic membrane, in the tip of a custom solid mold, and concluded that auditory temperatures could not be used to estimate core temperature due to the modifying influence of skin temperature on the measured values. These conclusions may have curtailed further research into temperature sensing systems in the ear. Ear-based thermometer products eventually emerged with the advent of the infrared temperature sensor that could take the temperature directly from the tympanic membrane without contact to the ear. The primary problem with tympanic membrane measurements has always been obtaining a direct field of view from the measurement sensor to the tympanic membrane through a narrow and often angular ear canal.

Temperature sensing from an ear-worn device presents many size and power constraints. Infrared thermopile sensors used for ear thermometry are housed in TO-46 form factor packages that are 5 mm in diameter. When combined with a speaker and a vent found in hearing aids, this 5 mm package is too large for most ears. This approach is challenging because it requires a means to get around the second bend (located deep inside the ear) in order to get a direct viewing angle of the tympanic membrane and about 12 other electronic components in order to be functional.

The inventors have realized that a problem to be solved in the art includes the ability to obtain absolute core temperate measurements and changes in temperature measurements from devices that can be inserted into and/or worn on or in the ear. An error (95% confidence interval) of +/−0.5° C. or less is desirable for absolute temperature. This is measured against a reference tool and is dependent on the location that the temperature is taken from, as well as the construction of the interface to the ear and a design which does not allow a draft to cause variability in the temperature readings. Additionally, in order to address this problem, the problem of compensating for the effect of changing environmental temperature around the wearer needs to be addressed and a rapid response to change in temperature is desirable for some applications.

In the present description, methods for measuring temperature from various devices, including an ear-worn device, a hand-held thermometer, and other devices with similar measurement capabilities, are described. The present description discloses positioning a sensor at a unique in-ear location for temperature sensing and methods of mounting the sensor to an ear-worn device or thermometer probe to improve accuracy and precision. The various methods involve using a thermistor to measure temperature from a particular location in the ear that is consistent with the highest temperature of the surface of the ear in areas that can contact an in-the-ear (ITE), in-the-canal (ITC), completely-in-canal (CIC), and invisible-in-the-canal (IIC) structure, or from another location of a device such as the receiver of a standard earbud hearing device or a temperature probe of a hand-held thermometer. Thermistor contact-sensors offer low cost, low power solutions which enable a continuously-worn ear device. The sensor can be used to measure absolute body temperature or trend of body temperature from an ear-worn device. Designs of the thermistor-to-ear device and thermistor-to-ear interfaces, designing for a draft-free temperature gradient across those interfaces, and a means of determining absolute temperature under changing environmental temperature and draft are described.

FIG. 1 is an illustration of a person's ear 10 and, in particular, the ear canal 22. The ear 10 illustrated in FIG. 1 shows a number of anatomical features near the earline 12, including the antitragus 14, concha 16, helix 18, and tragus 20. The ear canal 22 includes a proximal section 21 between the tragus 20 and a first bend 24 of the canal 22. A middle section 27 is shown between the first bend 24 and a second bend 26 of the canal 22. A distal section 29 is shown between the second bend 26 and an ear drum 28.

Embodiments are directed to devices and methods that measure temperature at a preferred location of the ear canal 22, from which absolute core body temperature can be calculated using a heat balance equation in accordance with various embodiments. Embodiments are directed to devices and methods that measure temperature at a preferred location of the ear canal 22 (and other locations within or external of the ear canal as described herein) using a temperature sensor(s) configured to sense conductive and/or convective heat, rather than radiative heat.

Figure 2:
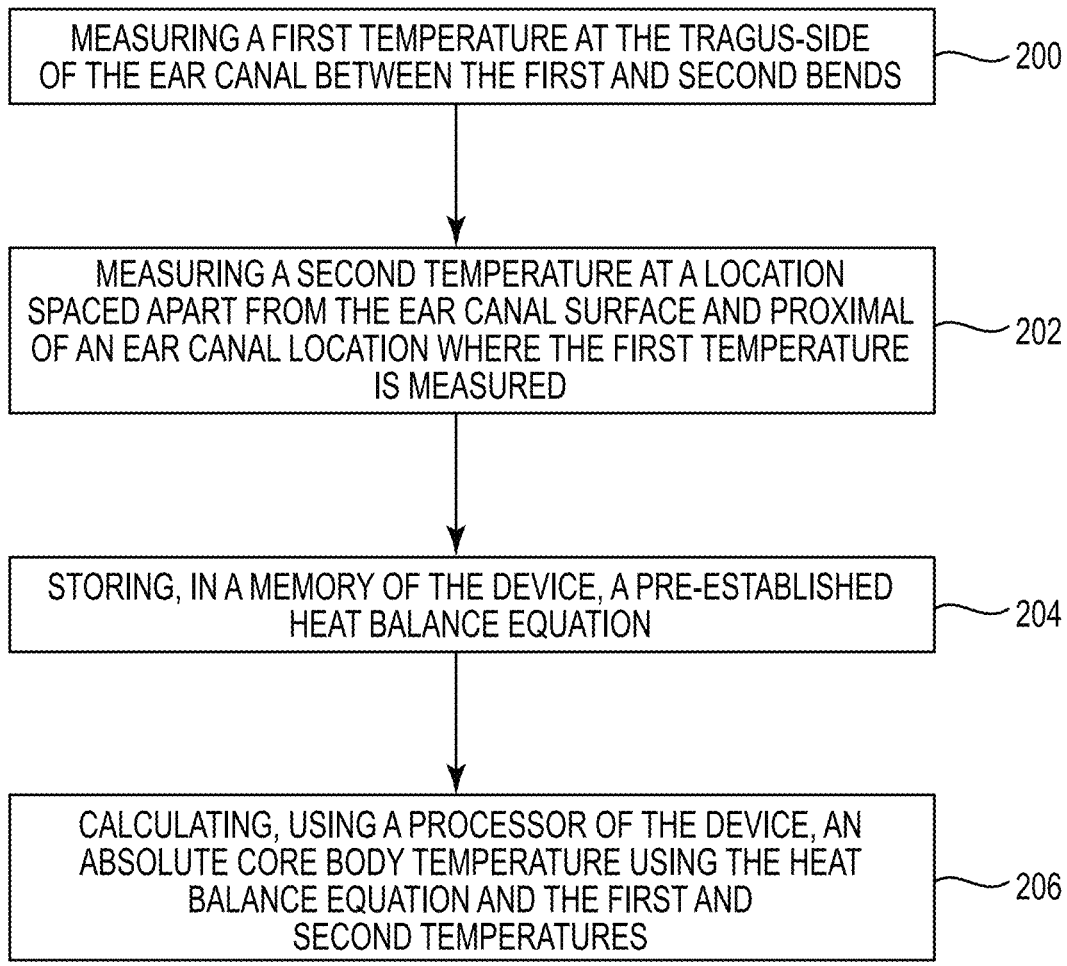
FIG. 2 is a method that can be implemented by devices described in the present disclosure in accordance with various embodiments.

FIG. 2 is a method that can be implemented by devices described in the present disclosure in accordance with various embodiments. With continued reference to FIG. 1, the method shown in FIG. 2 involves measuring 200 a first temperature at the tragus-side 20 of the ear canal 22 between the first bend 24 and the second bend 26. The method involves measuring 202 a second temperature at a location spaced apart from a surface of the ear canal 22 and proximal of an ear canal location where the first temperature is measure (in an outer ear direction). For example, the second temperature can be measured at a location spaced apart from the ear canal surface and exterior to the first bend 24 (e.g., within the ear canal or other outer ear location or exterior of the ear). By way of further example, the second temperature can be measured at a location spaced apart from the ear canal surface and exterior to the second bend 26 and interior to the first bend 24. The first and second temperatures are preferably indicative of conductive and/or convective heat, rather than radiative heat. The method further involves storing 204, in a memory of the device, a pre-established heat balance equation. The method also involves calculating 206, using a processor of the device, an absolute core body temperature using the heat balance equation and the first and second temperatures.

FIGS. 3A and 3B show a representative ear-worn device positioned relative to a preferred location of the ear canal from which temperature measurements can be obtained in accordance with various embodiments. The ear-worn device 300 is configured as an ITE device comprising an enclosure 302. The enclosure 302, also referred to herein as a shell, is configured for insertion into the ear canal 22 and includes a distal end 304 and a proximal end 306. The terminus of the distal end 304 includes a tip 305, and a terminus of the proximal end 306 includes a faceplate 308, which may include a vent 310. The distal end 304 is configured to extend at least beyond the first bend 24. In the case of an ITE device 300 shown in FIGS. 3A and 3B, the tip 305 of the distal end 304 terminates prior to the second bend 26. In other device configurations (e.g., CIC, IIC), the tip 305 can terminate beyond the second bend 26.

Through experimentation, it was determined by the inventors that there exists a preferred location within the left and right ear canals 22 for making temperature measurements particularly useful for calculating absolute core body temperature. This preferred location (e.g., the "key" location) of the ear canal 22 was identified as "Location 2," which is shown as a solid dot in FIGS. 3A and 3B. It was determined by the inventors that Location 2 is the warmest region in the ear canal 22 that is adjacent to areas reachable from the surface of a temperature sensing device, such as the ear-worn device 300 or a hand-held thermometer. Location 2 is located on the ventral side of the ear canal 22 just past the first bend 24 and before the second bend 26. More particularly, Location 2 is interior to the tragus "flat" area, interior to the first bend 24, and exterior to the second bend 26 on the ventral side of the ear canal 22. Preferably, Location 2 is a location of the ear canal 22 between the first and second bends 24, 26 that is close (e.g., nearest) to the superficial temporal artery branch of the external carotid artery. Location 2 is a preferred location of the ear canal 22 for measuring temperature from an ITE, ITC, CIC, IIC device or any other housing/enclosure, device or earbud that includes that location.

According to various embodiments, a distal temperature sensor is situated at a location of the enclosure 302 that can measure the temperature of ear canal tissue at or immediately adjacent Location 2. More particularly, the distal temperature sensor is situated at a location of the enclosure 302 that faces a tragus-side 20 of the ear canal 22 between the first and second bends 24, 26 when the enclosure 302 is fully inserted into the ear canal 22. The distal temperature sensor is configured to produce a first temperature signal. A proximal temperature sensor is situated at a location of the enclosure 302 spaced apart from a surface of the ear canal 22 and proximal of the distal temperature sensor in an outer ear direction. For example, the proximal temperature sensor can be situated on the faceplate 308. As will be discussed hereinbelow, an absolute core body temperature can be calculated using a heat balance equation and the first and second temperature signals. In this and other embodiments disclosed herein, the distal and proximal temperatures sensors are preferably sensors configured to sense conductive and/or convective heat, rather than radiative heat (e.g., non-IR sensors), representative examples of which are described hereinbelow.

A prototype of an ITE device similar to that shown in FIGS. 3A and 3B was developed for evaluation. The prototype ITE device included a temperature sensor situated at a preferred site (referred to herein as site 2) of the device enclosure for sensing temperature at Location 2 of the ear canal. More particularly, the prototype ITE device included a low power, small form factor thermistor configured to measure human temperature in environmental temperatures of 5° C. to 42° C. and draft. The prototype ITE device further included a closed faceplate in order to be resistant to draft. Using a methodology disclosed herein, the prototype ITE device utilized the temperature gradient across the ear to calculate absolute temperature within +/−0.5° C. without individual calibration.

Figure 3D:
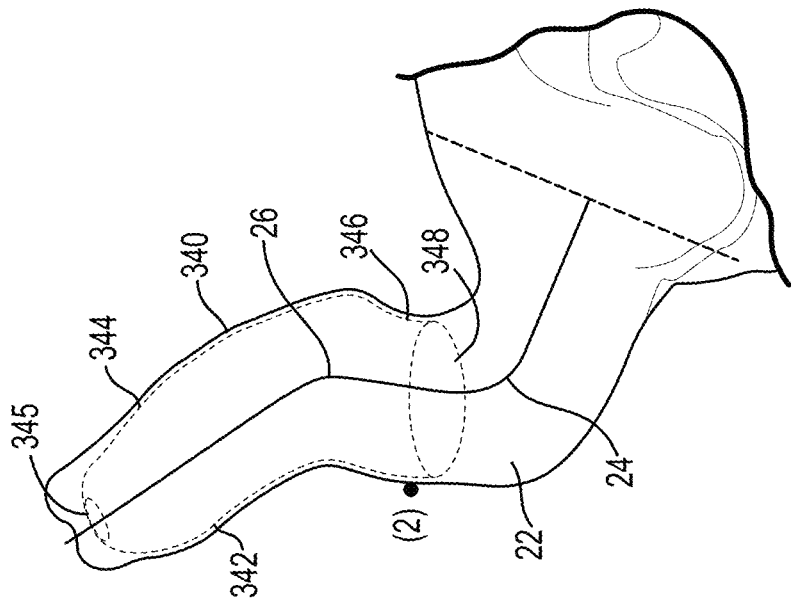
FIG. 3D shows a representative ear-worn device positioned relative to a preferred location of the ear canal from which temperature measurements can be obtained in accordance with various embodiments.
Figure 3C:
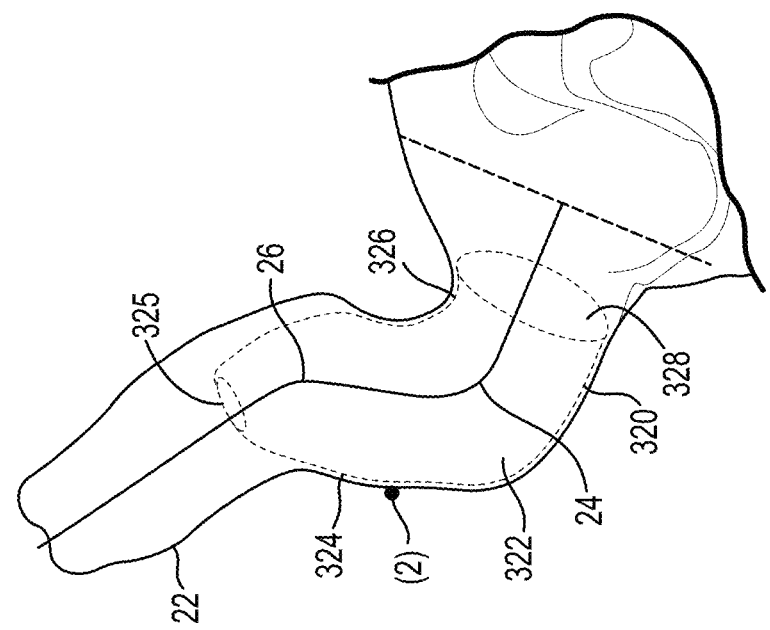
FIG. 3C shows a representative ear-worn device positioned relative to a preferred location of the ear canal from which temperature measurements can be obtained in accordance with various embodiments.

FIG. 3C shows a representative ear-worn device positioned relative to a preferred location of the ear canal 22 from which temperature measurements can be obtained in accordance with various embodiments. The ear-worn device 320 is configured as a CIC device comprising an enclosure 322. The enclosure 322 is configured for insertion into the ear canal 22 and includes a distal end 324 and a proximal end 326. The terminus of the distal end 324 includes a tip 325, and a terminus of the proximal end 326 includes a faceplate 328. The distal end 324 is configured to extend beyond the second bend 26, with a tip 325 of the distal end 324 terminating prior to the tympanic membrane. The faceplate 328 typically terminates exterior of the first bend 24 and interior of the aperture of the ear canal 22. A distal temperature sensor is situated at a location of the enclosure 322 that can measure the temperature of ear canal tissue at or immediately adjacent Location 2. A proximal temperature sensor is situated at a location of the enclosure 322 spaced apart from a surface of the ear canal 22 and proximal of the distal temperature sensor in an outer ear direction. For example, the proximal temperature sensor can be situated on the faceplate 328 or a location between the faceplate 328 and the distal temperature sensor. An absolute core body temperature can be calculated using a heat balance equation and first and second temperature signals produced by the distal and proximal temperature sensors. It is noted that in this and other embodiments, the heat balance equation can characterize a temperature gradient of the ear for a population of persons over a range of ambient temperatures.

FIG. 3D shows a representative ear-worn device positioned relative to a preferred location of the ear canal 22 from which temperature measurements can be obtained in accordance with various embodiments. The ear-worn device 340 is configured as an IIC device comprising an enclosure 342. The enclosure 342 is configured for insertion into the ear canal 22 and includes a distal end 344 and a proximal end 346. The terminus of the distal end 344 includes a tip 345, and a terminus of the proximal end 346 includes a faceplate 348. The distal end 344 is configured to extend beyond the second bend 26, with a tip 345 of the distal end 344 terminating prior to the tympanic membrane. The faceplate 348 terminates exterior of the second bend 26 and interior of the first bend 24. A distal temperature sensor is situated at a location of the enclosure 342 that can measure the temperature of ear canal tissue at or immediately adjacent Location 2. A proximal temperature sensor is situated at a location of the enclosure 342 spaced apart from a surface of the ear canal 22 and proximal of the distal temperature sensor in an outer ear direction. For example, the proximal temperature sensor can be situated on the faceplate 348 or a location between the faceplate 348 and the distal temperature sensor. An absolute core body temperature can be calculated using a heat balance equation and first and second temperature signals produced by the distal and proximal temperature sensors.

Figure 3E:
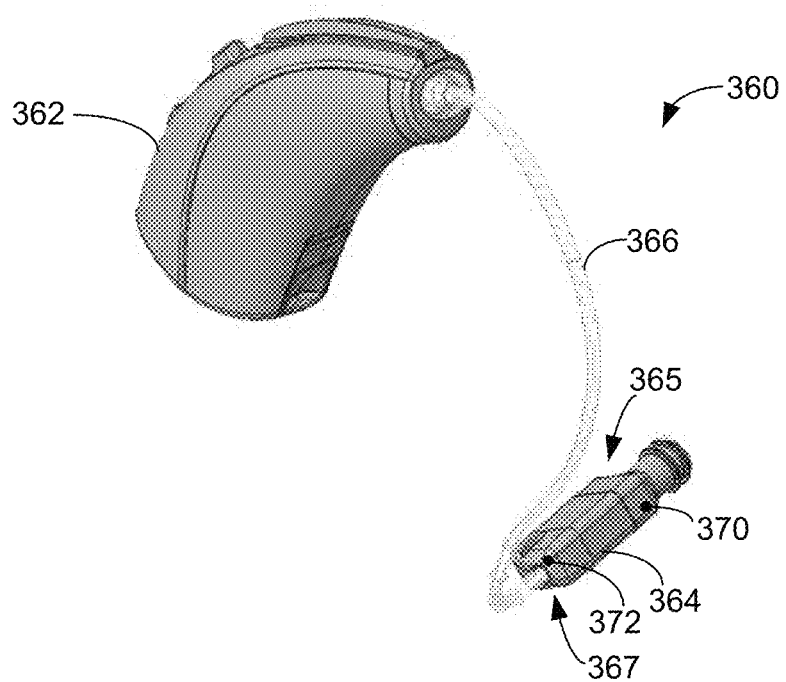
FIG. 3E shows a representative ear-worn device positioned relative to a preferred location of the ear canal from which temperature measurements can be obtained in accordance with various embodiments.
Figure 3F:
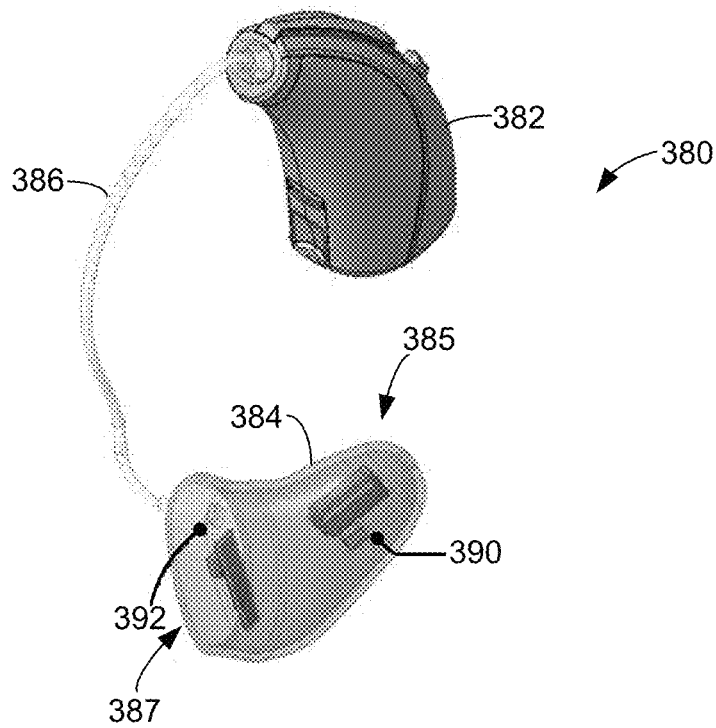
FIG. 3F shows a representative ear-worn device positioned relative to a preferred location of the ear canal from which temperature measurements can be obtained in accordance with various embodiments.

FIGS. 3E and 3F show representative ear-worn devices which include an in-ear component that can be positioned relative to a preferred location of the ear canal from which temperature measurements can be obtained in accordance with various embodiments. The ear-worn devices 360, 380 are configured as RIC devices. The ear-worn device 360 is representative of a standard RIC implementation, which includes a standard receiver 364 coupled to a case 362 via a cable 366. The ear-worn device 380 is representative of a custom RIC implementation, which includes a custom receiver 384 (molded to the wearer's ear canal) coupled to a case 382 via a cable 386. The case 362, 382 is configured for positioning behind the ear of the wearer, and the receiver 364, 384 is configured for positioning in the ear canal. The receiver 364, 384 includes a loudspeaker, while other electronics are housed in the case 362, 382.

The receiver 364, 384 includes an enclosure configured for insertion into the ear canal and includes a distal end 365, 385 and a proximal end 367, 387. The distal end 365, 385 is configured to extend beyond the first bend, and typically terminates prior to the second bend. A distal temperature sensor 370, 390 is situated at a location of the receiver 364, 384 (e.g., a forward location) that can measure the temperature of ear canal tissue at or immediately adjacent Location 2. A proximal temperature sensor 372, 392 is situated at a location of the receiver 364, 384 spaced apart from a surface of the ear canal and proximal of the distal temperature sensor 370, 390 in an outer ear direction (e.g., a rearward location). For example, the proximal temperature sensor 372, 392 can be situated at or near the rear enclosure surface of the receiver 364, 384 proximate the cable 366, 386. An absolute core body temperature can be calculated using a heat balance equation and first and second temperature signals produced by the distal temperature sensor 370, 390 and the proximal temperature sensor 372, 392.

Figure 4B:
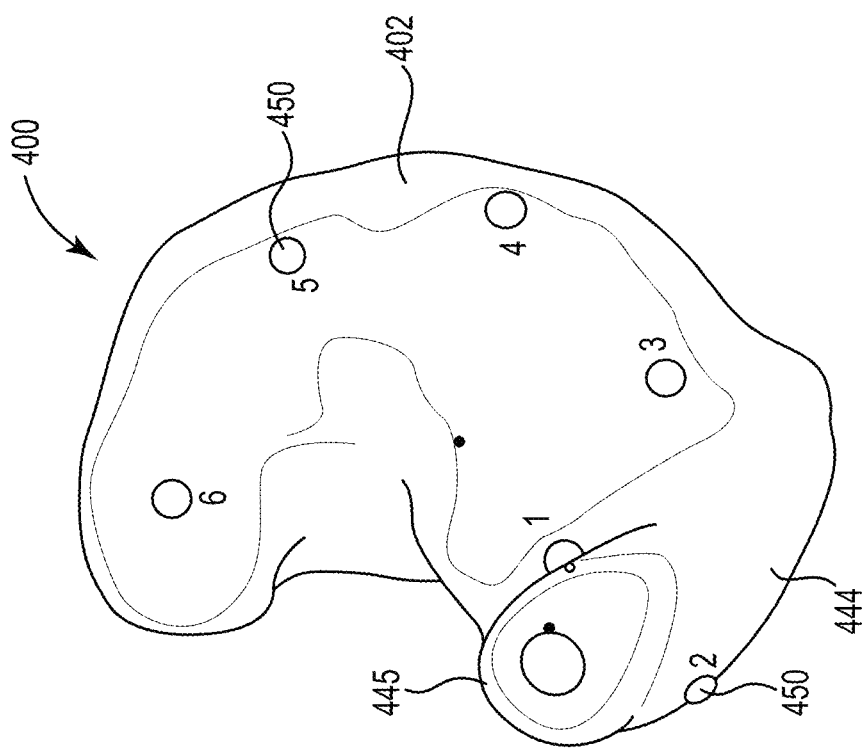
FIGS. 4A and 4B show different views of an ear-worn device developed by the inventors to determine the preferred location of the ear canal from which temperature measurements can be obtained in accordance with various embodiments.
Figure 4A:
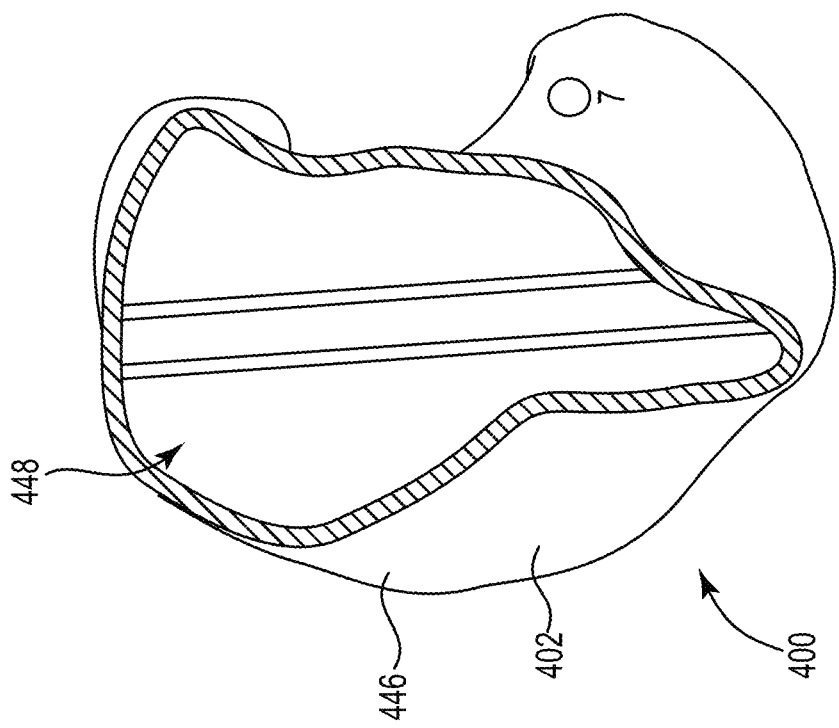

FIGS. 4A and 4B show different views of an ear-worn device 400 developed by the inventors to determine the preferred location of the ear canal from which temperature measurements can be obtained in accordance with various embodiments. The ear-worn device 400 is configured as an ITE device comprising an enclosure 402 which includes a distal end 444, terminating at a distal tip 445, and a proximal and 446, terminating at a faceplate region 448 (faceplate not shown). A number of temperature sensors 450 are distributed at various sites on the surface of the enclosure 402. In the particular configuration shown in FIGS. 4A and 4B, a total of seven temperature sensors 450, implemented as thermistors, were positioned at sites 1-7 for left and right ear-worn devices 400. Left and right ear-worn devices 400 were inserted into the left and right ears of two human test subjects.

Temperature data was acquired from the temperature sensors 450 at each of the seven sites of the left and right ear-worn devices 400 for the two test subjects. This temperature data is graphically presented in FIG. 5. Curves 502 and 504 show left and right ear temperature data for test subject 1, and curves 512 and 514 show left and right ear temperature data for test subject 2. The temperature data shown in FIG. 5 reveals that the highest ear temperatures for test subjects 1 and 2 were measured at site 2, which aligns with ear-canal Location 2 in the previous figures. According to various embodiments, a productized implementation of the ear-worn device 400 includes at least one temperature sensor at site 2 for measuring temperature at Location 2 of the ear canal. In some embodiments, in addition to a temperature sensor at site 2, the ear-worn device 400 includes one or more temperature sensors situated at one or more additional sites (e.g., site 7 or at the faceplate region 448). It is noted that an adequate temperature measurement sufficient for purposes of calculating absolute core body temperature can be obtained from a temperature sensor positioned at a site other than site 2 (e.g., site 1), but that measuring temperature at site 2 is preferred.

As was discussed above, the ear-worn device 400 shown in FIGS. 4A and 4B (and the devices of other figures) can include one or more temperature sensors implemented as thermistors. Thermistors offer a low cost, low power, small form factor solution which enables a continuously-worn ear-level device, such as a hearing aid. Various types of thermistors can be incorporated into the ear-worn devices and other temperature sensing devices disclosed herein. Preferred thermistors are those having a negative temperature coefficient (NTC), although those having a positive temperature coefficient (PTC) can be used in some implementations.

Figure 6:
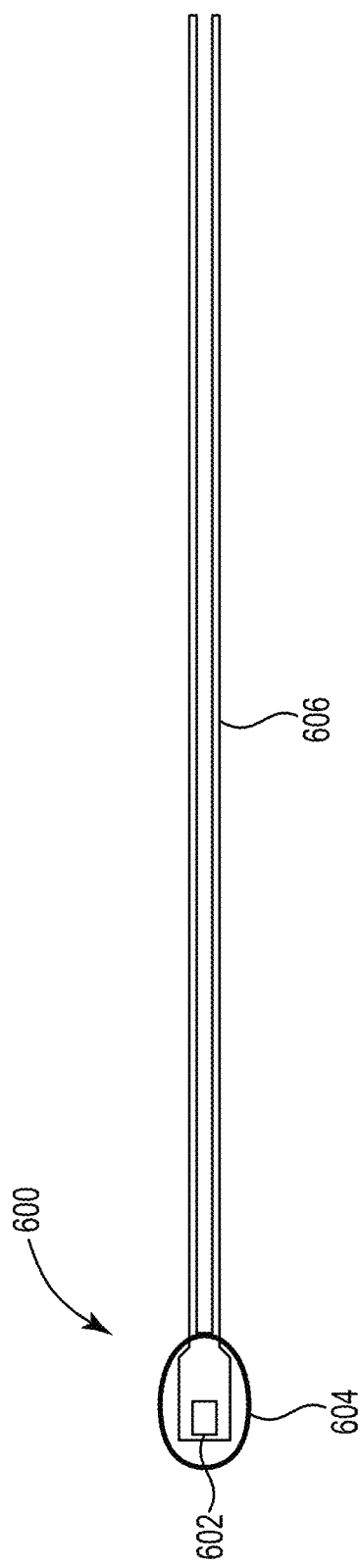
FIG. 6 is an illustration of a thermistor suitable for incorporation in an ear-worn device or other temperature sensing device in accordance with various embodiments.
Figure 7:
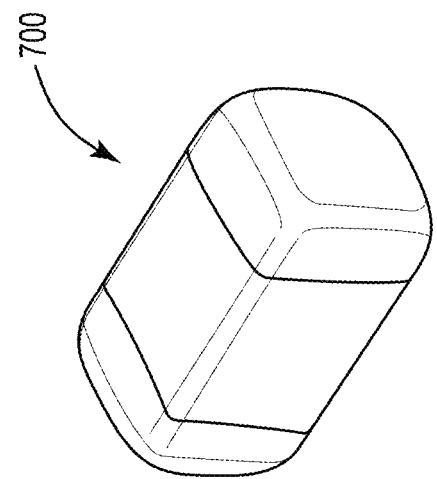
FIG. 7 is an illustration of a thermistor suitable for incorporation in an ear-worn device or other temperature sensing device in accordance with various embodiments.

For example, and with reference to FIG. 6, a temperature sensing device of the present disclosure can incorporate a glass encapsulated thermistor 600, which includes a chip 602 (e.g., a negative temperature coefficient (NTC) chip) encapsulated within a bead of glass 604. Leads 606 (e.g., dumet leads) are coupled to the chip 602 and to circuitry within the temperature sensing device. By way of further example, FIG. 7 shows a representative SMD (surface mount device) thermistor 700, which can be used for temperature sensing alone or in combination with other types of thermistors or temperature sensors. Other temperature sensors can be used in a temperature sensing device of the present disclosure, including thermocouples, resistance temperature detectors (RTDs), digital thermistors, and other types of resistance temperature sensors. An ear-worn device or a temperature sensing device of the present disclosure can incorporate any or a combination of these types of temperature sensors. For example, passive thermistors as small as 1.6 mm×0.8 mm×0.8 mm that only require one additional resistor can be used, which are particularly useful for incorporation in an ear-worn device.

In an ear-worn device or other temperature sensing device that incorporates a thermistor, the leads or contacts of the thermistor are coupled to an analog-to-digital converter (ADC) and a processor. Changes in thermistor resistance correspond to changes in temperature. Thermistor resistance can be converted to temperature by the processor using the well-known Steinhart-Hart equation (e.g., via a lookup table). The Steinhart-Hart equation is considered the best mathematical expression for the resistance-temperature relationship of NTC thermistors. The coefficients of the Steinhart-Hart equation vary with thermistor type and are typically provided by the manufacturer or readily derivable.

Figure 8:
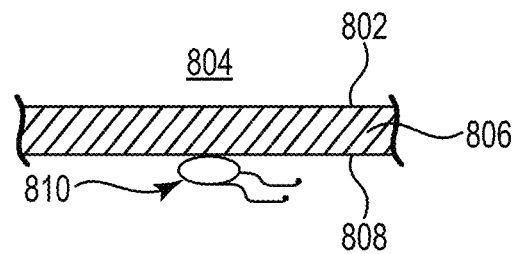
FIG. 8 is a sectional view of a temperature sensor mounted to an enclosure or shell of an ear-worn device or other temperature sensing device in accordance with various embodiments.

A thermistor or other temperature sensor can be mounted on, to or supported by the enclosure of an ear-worn device or other temperature sensing device in a variety of ways, several representative examples of which are described below. It is understood that the embodiments described below and elsewhere herein can incorporate any type of thermistor or temperature sensor. In a first embodiment, the absolute core temperature can be obtained to within an error (95% confidence interval) of +/−0.5° C. by mounting the thermistor on the inside surface of the shell material of the ear device that is free from draft by using a faceplate or insulating material layer in combination with a second thermistor to calculate the heat balance. The heat balance may be based on an oral or other reference thermometer. For example, and with reference to FIG. 8, a portion of the enclosure or shell 802 of an ear-worn device or other temperature sensing device is illustrated in contact with the skin-side 804 of an ear. The shell 802 is formed from a material or matrix 806, such as methacrylate, having a specified thermal conductivity. In the embodiment shown in FIG. 8, a thermistor 810 (e.g., a glass encapsulated thermistor) is mounted on the inside surface 808 of the ear device matrix 806 with a higher thermal conductivity adhesive than the thermal conductivity of the ear device matrix 806, such as a liquid curable adhesive, to minimize thermal resistance at the mounting site thereby minimizing temperature measurement error associated with the mounting of the thermistor. It is noted that the actual thermistor reading can be obtained to within an error of +/−0.1° C.

Figure 9:
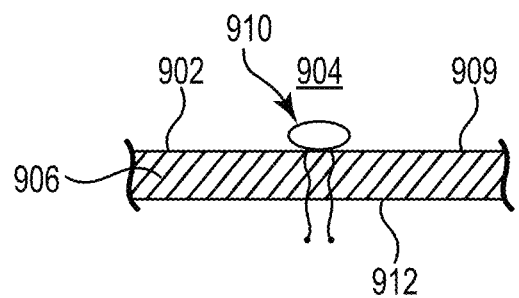
FIG. 9 is a sectional view of a temperature sensor mounted to an enclosure or shell of an ear-worn device or other temperature sensing device in accordance with various embodiments.

In a second embodiment, the thermistor can be placed directly on the surface of the ear device that is enclosed and draft free or insulated from draft on the backside so that the thermistor is in direct contact with the skin of the ear. For example, and with reference to FIG. 9, a portion of the enclosure or shell 902 of an ear-worn device or other temperature sensing device is illustrated in contact with the skin side 904 of an ear. The shell 902 can be formed from a material or matrix 906 described above. In the embodiment shown in FIG. 9, a thermistor 910 (e.g., a glass encapsulated thermistor) is mounted directly on the outer surface 909 of the ear device matrix 906. It was found that the ear skin interface-surface mounted thermistor 910 can measure absolute core temperature to within an error of +/−0.5° C. with respect to a temporal or other reference thermometer. The embodiment shown in FIG. 9 allows a more rapid response to changes in body temperature due to more direct contact with the skin 904.

Figure 10:
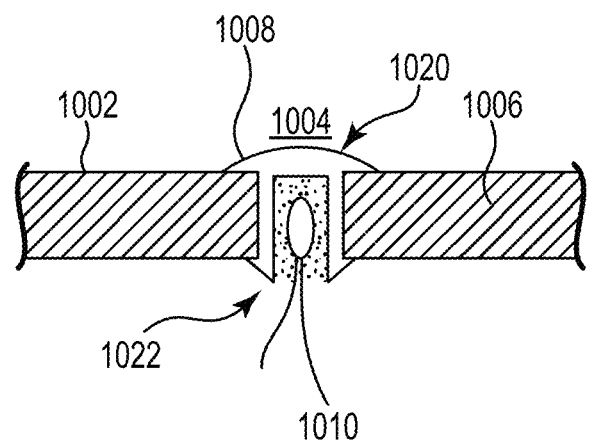
FIG. 10 is a sectional view of a temperature sensor mounted to an enclosure or shell of an ear-worn device or other temperature sensing device in accordance with various embodiments.

In a third embodiment, the interface between the thermistor and the ear can be designed to increase (e.g., maximize) contact and thermal conductivity with the ear skin. As is shown in FIG. 10, this can be accomplished using an insert 1020 which can be installed in the ear device matrix 1006 (e.g., integrated as part of the shell 1002). The insert 1020 forms a gradually sloping dome 1008 that protrudes into the skin 1004 even during jaw/ear movement. The thermistor 1010 (e.g., a glass encapsulated thermistor) can be mounted in the insert 1020 using a liquid curable adhesive 1022 that has a thermal conductivity higher than the ear device matrix 1006 so that heat flux is increased at the insert location. The domed insert 1020 can be made of any material, but preferably polymer or metal material. The contour of the insert 1020 can be flat, domed or conformal to the shell 1002 or any other shape.

Figure 11:
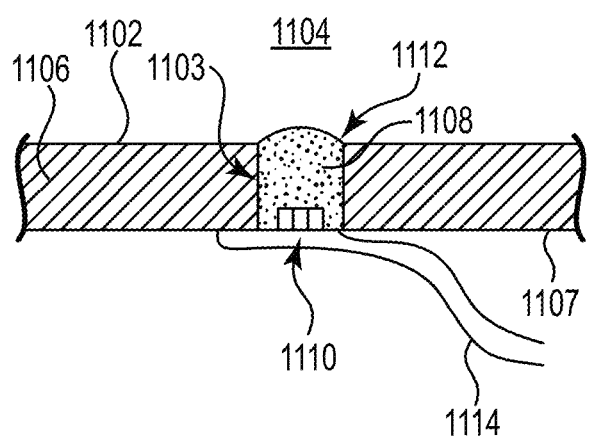
FIG. 11 is a sectional view of a temperature sensor mounted to an enclosure or shell of an ear-worn device or other temperature sensing device in accordance with various embodiments.

In a fourth embodiment, and as shown in FIG. 11, the thermistor 1110 (e.g., an SMD thermistor) can be placed in or under a hole 1103 in the ear device matrix 1106 of the shell 1102. The hole 1103 can be filled with material 1108. The diameter of the hole 1103 and the volume of the material 1108 dispensed can be used to control the height of the fill material 1108 such that it forms a rounded structure 1112 that protrudes into the skin 1104 of the ear even under movement. The dome shape of the rounded structure 1112 can be formed by surface tension of the fill material 1108. The thermal conductivity of the fill material 1108 can be altered to govern whether the device performance matches a temporal or oral reference thermometer and to govern the response of the device to temperature change. In FIG. 11, a flexible or rigid circuit 1114 is incorporated to electrically connect with the thermistor 1110. A portion of the circuit 1114 that connects to the thermistor 1110 can be secured to the inner surface 1107 of the ear device matrix 1106 using an electrically conductive adhesive.

Figure 12:
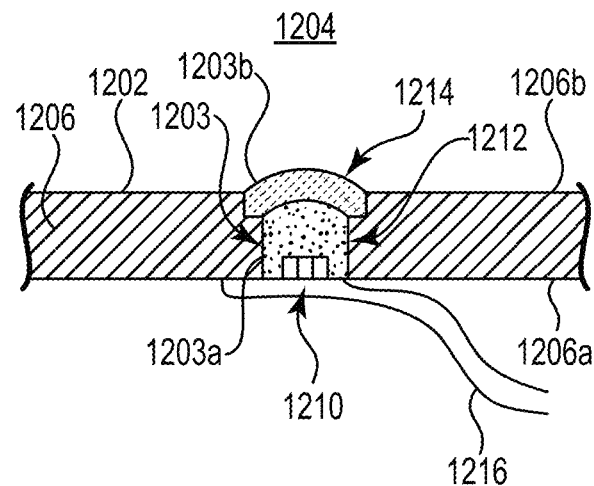
FIG. 12 is a sectional view of a temperature sensor mounted to an enclosure or shell of an ear-worn device or other temperature sensing device in accordance with various embodiments.

In a fifth embodiment, and as illustrated in FIG. 12, the matrix or material 1206 of the shell 1202 includes a cylindrical cavity 1203 within which the thermistor 1210 (e.g., an SMD thermistor) is situated. The thermistor 1210 is electrically connected to a flexible or rigid circuit 1216. The cylindrical cavity 1203 is filled with a composite of materials (e.g., liquid fill materials) having different thermal conductivity. The cylindrical cavity 1203 comprises a narrow cavity portion 1203*a* extending from an inner surface 1206*a* of the ear device matrix 1206 and a wide cavity portion 1203*b* extending from an outer surface 1206*b* of the ear device matrix 1206. The narrow cavity portion 1203*a* is filled with a first fill material 1212 having a first thermal conductivity, and the wide cavity portion 1203*b* is filled with a second fill material 1214 having a second thermal conductivity. The difference in diameter of the narrow and wide cavity portions 1203*a*, 1203*b* allows the liquid fill materials 1212, 1214 to be deposited sequentially using the inside edge of the cylindrical cavity 1203 to confine the liquid material. The narrow and wide cavity portions 1203*a*, 1203*b* can be formed into the wall of the shell 1202 during fabrication or can be drilled in later or a combination of both.

Figure 13:
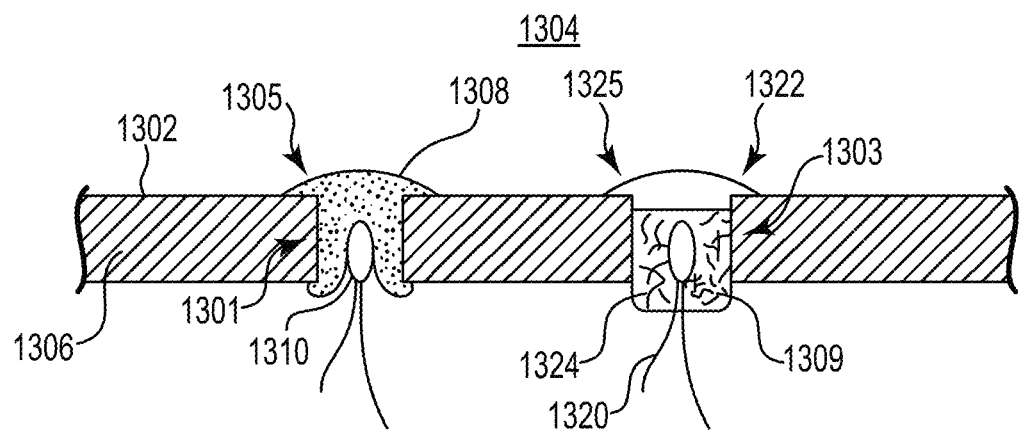
FIG. 13 is a sectional view of temperature sensors mounted to an enclosure or shell of an ear-worn device or other temperature sensing device in accordance with various embodiments.

In a sixth embodiment, and as shown in FIG. 13, a thermistor 1310 (e.g., a glass encapsulated thermistor) can be situated within a solid insert 1305 inserted into a cavity 1301 in the matrix or material 1306 of the shell 1302. The solid insert 1305 can be formed from solid fill material 1308, such as foam or fibrous material. The fill material 1308 can be dome or flat shaped on one side to interface with skin 1304 of the ear. According to another configuration, a vessel 1324 can be installed within a cavity 1303 in the ear device matrix 1306. The vessel 1324 can contain loose insulating fill material 1309, such as foam or fibrous material, within which the thermistor 1320 (e.g., a glass encapsulated thermistor) is embedded. A thermally conductive cap 1322 covers the vessel 1324 and is configured to contact the skin 1304 of the ear. The side of the cap 1322 that interfaces with the skin 1304 of the ear can be dome or flat shaped. The thermistor 1320 is preferably positioned within the vessel 1324 so as to contact the thermally conductive cap 1322.

A highly thermally conductive top structure or material adhered to the thermistor using thermally conductive adhesive over a thermistor surrounded by material with low thermal conductivity can be advantageous in selectively obtaining the temperature from a given localized site. The thermal conductivity of the shell/matrix material is typically in the range of 0.1 to 0.3 W/mK. The thermal conductivity of the insulating material must be lower than that of the shell/matrix material. Typical values are in the range of 0.02-0.016 W/mK. The thermal conductivity of the highly thermally conductive material will exceed that of the base shell/matrix material and will preferably be at least 4 times that value or 0.8 W/mK or greater. Extending the insulation below the thermistor will eliminate or reduce the need to provide a draft free inner shell surface.

Figure 14:
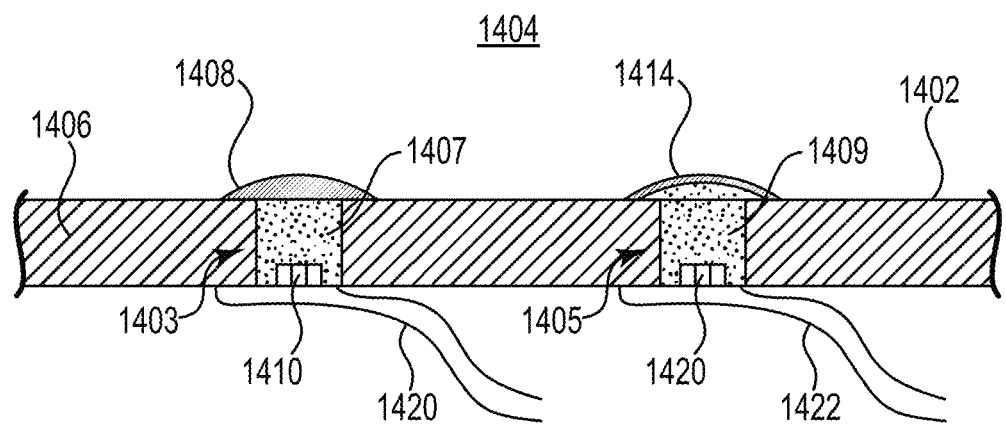
FIG. 14 is a sectional view of temperature sensors mounted to an enclosure or shell of an ear-worn device or other temperature sensing device in accordance with various embodiments.

In a seventh embodiment, and as illustrated in FIG. 14, a cavity 1403 is formed in the ear device matrix 1406 of the shell 1402. In one configuration, a thermistor 1410 (e.g., an SMD thermistor) is positioned within the cavity 1403 and electrically connected to a flexible or rigid circuit 1420 as discussed previously. The cavity 1403 is capped with a dome shaped concave (or flat) structure 1408. Air, another gas (e.g., an inert gas) or material 1407 is captured in cavity 1403. For example, an inert fill gas 1407 can enhance the reliability of the thermistor 1410. The inert fill gas 1407 can also be used with an open or woven fill material. In another configuration, a thermistor 1420 (e.g., an SMD thermistor) is positioned within a cavity 1405 and electrically connected to a flexible or rigid circuit 1422 as discussed previously. The cavity 1405 is capped with a dome shaped concave (or flat) structure 1414. An interface of the ear device matrix 1406 between the cap structure 1414 and the cavity 1405 is porous or perforated, allowing the fill gas and/or fill material to fill a void between the cap structure 1414 and the ear device matrix 1406.

Figure 15:
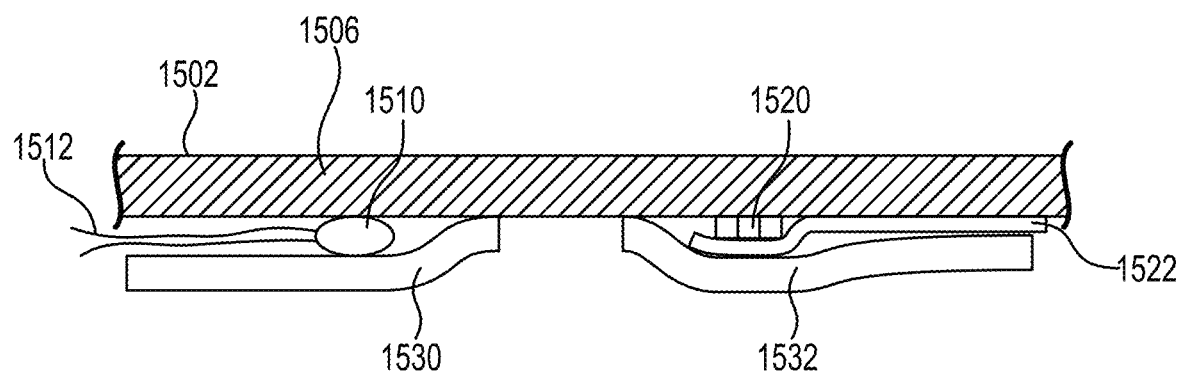
FIG. 15 is a sectional view of temperature sensors mounted to an enclosure or shell of an ear-worn device or other temperature sensing device in accordance with various embodiments.

In an eighth embodiment, and as illustrated in FIG. 15, a thermistor 1510 (e.g., a glass encapsulated thermistor with leads 1512) is positioned between two solid or solid structured materials 1506 and 1530 of the ear device. As illustrated, the thermistor 1510 is positioned between a solid top structure 1506 and a bottom structure or material 1530, such as a woven insulator. FIG. 15 also shows another thermistor 1520 (e.g., an SMD thermistor) positioned between two solid or solid structured materials 1506 and 1532 of the ear device. The top structure 1506 can be the ear device matrix or other structure of the ear device. In other configurations, the thermistor 1510, 1520 is positioned between the bottom structure of material 1530, 1532 and a configuration identified in any of embodiments 3 through 7 above. The primary function of the configurations shown in FIG. 15 is to provide a draft barrier or a barrier from temperature being generated by other components of the ear device in the circuit. This design also allows an open design structure that does not require a faceplate as a draft barrier. The bottom structure of material 1530, 1532 can be heat laminated or adhered with adhesive over the thermistor 1510, 1520.

In a ninth embodiment, the material on the ear side surface of the shell in an area over or around the temperature sensor can be coated using a thermally conductive adhesive or a metal in order to widen the area from which temperature is preferentially acquired from. The metal can be deposited using laser direct structuring (LDS), electroplating, PVD, CVD or any other metal deposition technique. The area of deposition can be defined manually, by using photolithography or by computer aided deposition. The high thermal conductive area can extend over inserts or fill areas or beyond those areas. The thermal conductivity of the material preferably exceeds that of the base shell material and is preferably at least 4 times that value or 0.8 W/mK or greater.

In a tenth embodiment, the insulating material can be extended to cover the entire inner surface of the shell matrix and used to encapsulate all of the electronic components in a protective and aesthetic manner. This method may or may not include an enclosed cavity and faceplate in the ear device. The insulating material can be heat laminated or adhered with adhesive onto the substrate material housing the thermistor.

In another aspect, the methods described in embodiments 1 and 3-9 above can be used to mount a thermistor in a faceplate or externally facing structure in order to obtain a measured temperature which can be used to derive a factor to compensate for changes in the ear canal temperature measured due to changes in environmental temperature or draft. In yet another aspect, the methods described in embodiments 1 and 3-9 above can be used to mount a thermistor in the ear-supported component of a behind-the-ear (BTE) or receiver-in-canal (RIC) device in order to obtain a measured temperature which can be used to derive a factor to compensate for changes in ear canal temperature measured via a thermistor mounted to a receiver/speaker due to changes in environmental temperature or draft.

EXAMPLE DEVICE EMBODIMENTS

Example A

In one aspect, the present description includes a device A that includes a thermistor at the key location (e.g., site 2) in a hearing device 1) inside, under or through the shell wall; 2) insulated from the housing; or 3) thermally connected to the housing; and/or attached directly using adhesives or attached via a subassembly (flex, circuit board, molded or otherwise formed structure).

Example B

In another aspect, the present description includes a device B that includes a thermistor at the faceplate of a hearing device, where: 1) the faceplate is sealed (i.e. required to function under changing environmental temperature and draft); 2) the thermistor is inside, under or through the wall; 3) the thermistor is insulated from the housing; 4) the thermistor is thermally connected to the housing; or 4) the thermistor is attached directly using adhesives or attached via a subassembly (flex, circuit board, molded or otherwise formed structure).

Example C

In yet another aspect, the present description includes a device C that includes both device A and B of Examples A and B above, and also a housing. In device C, the housing may be 1) filled with a material (solid, gas or solidified liquid) that is thermally insulated or conductive; 2) plastic (clear or opaque) and any color; 3) comprising a vent; 4) open, where one or more sides of the formed structure are made of a material (solid or solidified liquid) that is placed into the housing (e.g., AP RIC); metal (e.g., titanium); coated with a low or high thermal emissivity material (metal, metal oxide, etc.) either on the internal surface or external surface; and/or a formable open mesh structure that is filled with a material or molded into a material to form the outer surfaces.

Example D

In another aspect, the present description includes a device D that comprises a biometric device that includes 1) a housing or structure that interfaces with the ear; 2) a thermistor attached at a location within the ear canal; 3) a second thermistor that resides at a location that is exposed to the environment; and 3) any of devices A, B, or C of Examples A, B, and C above.

Example E

In yet another aspect, the present description includes a device E that comprises two thermistors mounted directly to the receiver of a standard earbud hearing device or a receiver of a receiver-in-canal (RIC) device. In some configurations, a first thermistors is mounted to the receiver to sense temperature at or near the skin of the ear (e.g., at or proximate Location 2), and a second thermistor is mounted on the receiver more exterior than the first thermistor (in an outer ear direction) and spaced away from the skin of the ear.

Example F

In another aspect, the present description includes a device F that includes any of devices A-E of Examples A-E above and a thermistor on a behind-the-ear device (e.g., such as in the manner of a BTE or RIC device).

Example G

In yet another aspect, the present description includes a device G that includes any of devices A-F of Examples A-F above in addition to an algorithm used to calculate absolute core body temperature from thermistor data.

Example H

In yet another aspect, the present description includes a device H, that includes any of devices A-G of Examples A-G above or a combination of those devices that further includes methods for individual correction for higher accuracy, where such methods may be based on: 1) temperature from a reference tool; 2) geometrical parameters from the ear impression and hearing aid; 3) material properties of the hearing aid and its components; and/or 4) factors derived from measurements taken by tympanometry.

Various embodiments are directed to ear-worn devices and other types of temperature sensing devices configured to calculate absolute core body temperature using a first temperature measurement taken at or near Location 2, a second temperature measurement taken proximal to the first temperature measurement location in the direction of the outer ear (e.g., within or external to the outer ear), and a heat balance equation. More particularly, absolute core body temperature can be calculated using a heat balance equation or a 4-point equation in order to derive a single equation that is valid from person-to-person to within +/−0.5° C. It is noted that, although not necessary, individual calibration can be used to improve the accuracy of an individual system by either entering two geometrical human parameters obtained from deep ear impression, one parameter from a standard ear impression and one from a tympanometry volume measurement or from calibration using a reference thermometer.

Figure 16A:
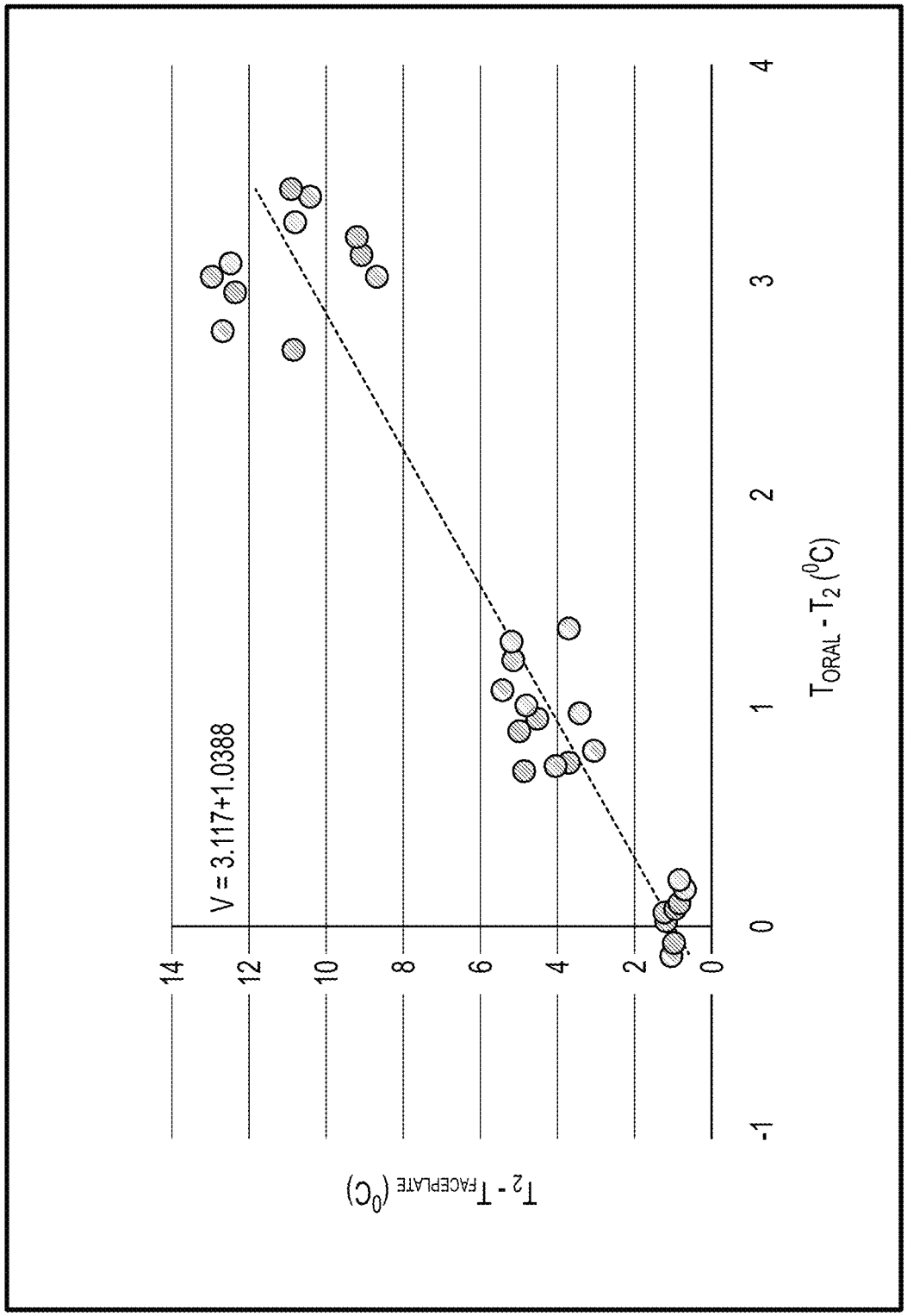
FIG. 16A is a graph illustrating a heat balance equation developed using an in-the-ear (ITE) shell in accordance with various embodiments.

FIG. 16A is a graph illustrating a heat balance equation developed using an ITE shell in accordance with various embodiments. Three temperature measurements are implicated in FIG. 16A: sensor 2 temperature ($T_2$ measured at or near Location 2 of the ear canal by a sensor at site 2 of the ITE shell), faceplate temperature ($T_{faceplate}$ measured at the faceplate of the ITE device by a sensor at the faceplate), and oral temperature ($T_{oral}$ measured using an oral reference thermometer). The Y-axis is given in terms of $T_2-T_{faceplate}$ in degrees Celsius, in the X-axis is given in terms of $T_{oral}-T_2$ in degree Celsius. Temperature can be measured at or near Location 2 and the faceplate over a range of environmental temperatures in order to derive the heat balance equation. A linear or logarithmic heat balance equation can be derived by plotting ($T_{oral}-T_2$) vs. ($T_2-T_{faceplate}$). The plot of ($T_{oral}-T_2$) vs. ($T_2-T_{faceplate}$) provides a consistent value when the ear is at equilibrium with the environment. After the heat balance equation is derived for a particular device, the heat balance equation is stored in a memory of an ear-worn device or other type of temperature sensing device. This heat balance equation can be used by the ear-worn or other type of temperature sensing device to calculate absolute core body temperature.

The heat balance equation used to calculate absolute core body temperature will vary based on a number of factors, including the configuration of the ear-worn device or other type of sensing device, the number and type of temperature sensors used, and the location of the temperature sensors on the device. For example, and with reference to FIG. 16B, two heat balance equations 1602 and 1604 are illustrated. As is evident in FIG. 16B, heat balance equations 1602 and 1604 have very different slopes. More particularly, heat balance equation 1602 has a much steeper slope than heat balance equation 1604. The ear-worn device associated with heat balance equation 1604 included two thermistors that were relatively close together (e.g. <10 mm). The ear-worn device associated with heat balance equation 1602 included two thermistors that were positioned further apart from one another (e.g. >20 mm).

Consider the following equation characterizing conductive heat flux through an infinite flat plate:

$$q=K(T_{inside}-T_{outside})/thx \qquad \text{Equation 1:}$$

where K is the thermal conductivity of the material, thx is the thickness of the plate, and $K_{int}$ and $K_{ext}$ are composite heat transfer coefficients. From Equation 1, two equations are provided below for the influx and efflux of heat from a sensor in between the innermost and outermost location in an ear.

$$q=K_{int}(T_{TM}-T_{int})/thx_{int} \qquad \text{Equation 2:}$$

$$q=K_{ext}(T_{int}-T_{ext})/thx_{ext} \qquad \text{Equation 3:}$$

where $thx_{ext}$ and $thx_{int}$ are the depth of the ear shell and the canal, respectively. At equilibrium, the influx and efflux of heat at the interior most location is equal so that:

$$K_{ext}(T_{int}-T_{ext})/thx_{ext}=K_{int}(T_{TM}-T_{int})/thx_{int} \qquad \text{Equation 4:}$$

and, $$(T_{int}-T_{ext})/(T_{TM}-T_{int})=K_{int}thx_{ext}/K_{ext}thx_{int} \qquad \text{Equation 5:}$$

Figure 16B:
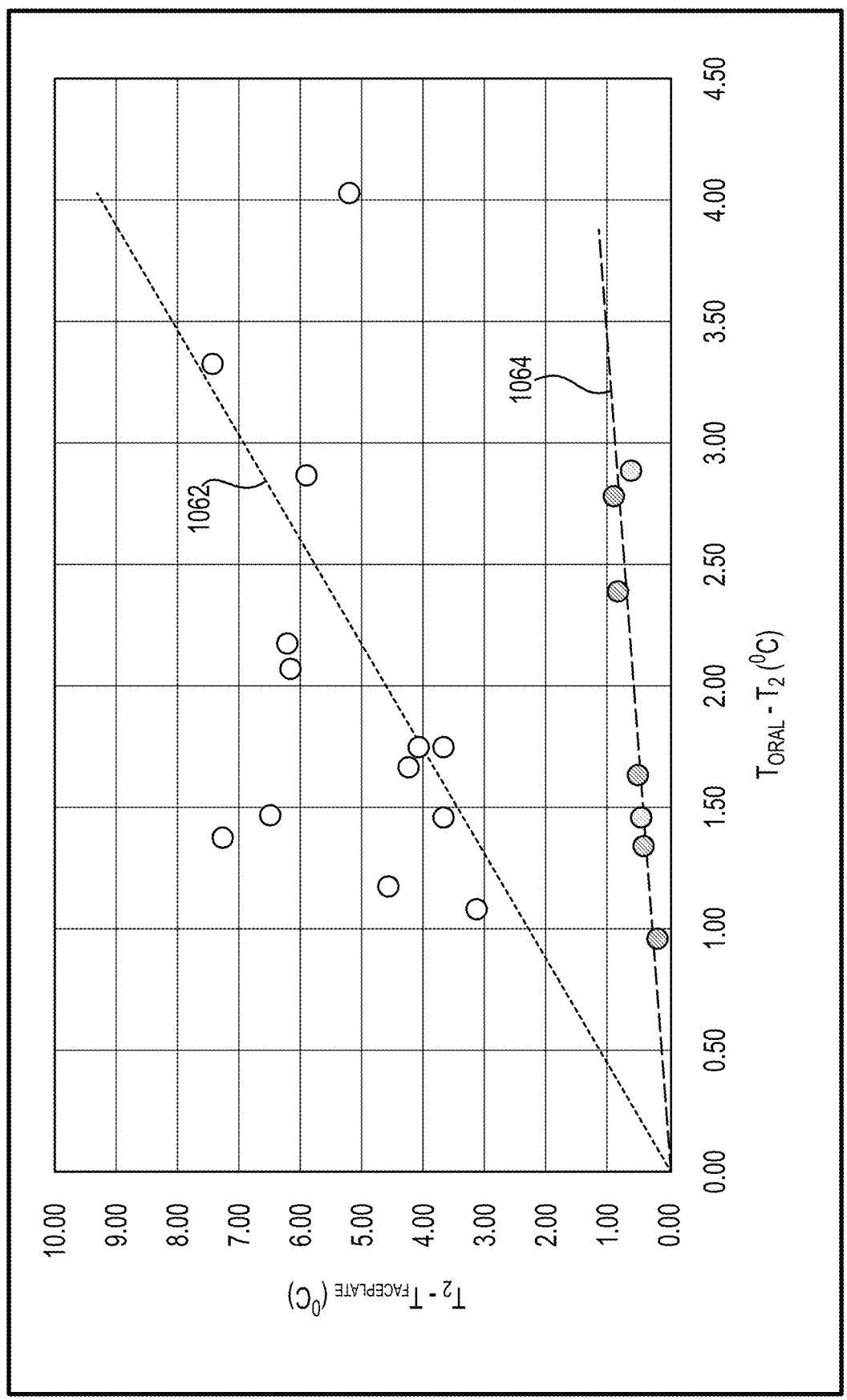
FIG. 16B shows graphs illustrating two different heat balance equations using ear-worn electronic devices having different spacing between temperature sensors in accordance with various embodiments.
Figure 17:
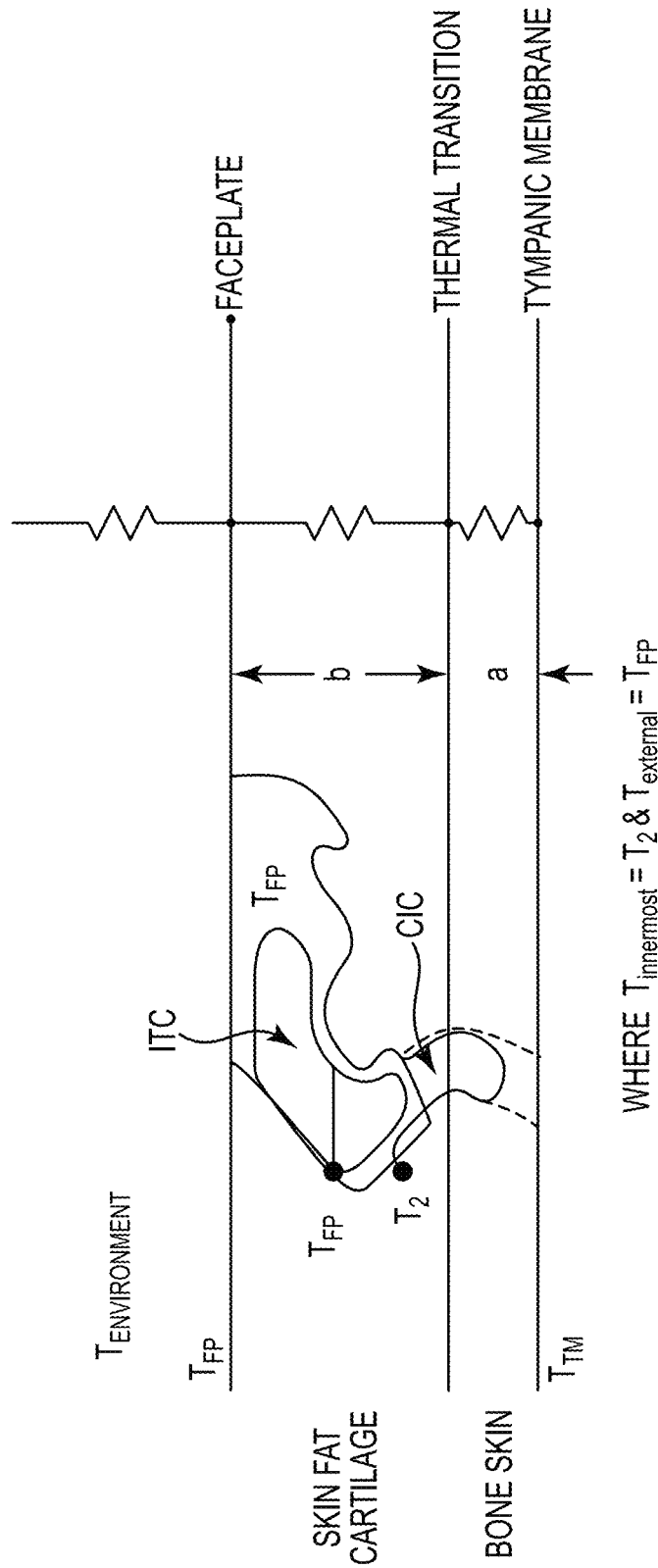
FIG. 17 is an illustration of a heat balance model used to calculate absolute core body temperature for a hearing device or other in-ear temperature sensor in accordance with various embodiments.

In light of the equations above and as shown in FIGS. 16A and 16B, a linear (or logarithmic) equation can be derived by plotting ($T_{oral}-T2$) vs. ($T2-T_{faceplate}$). FIG. 17 is an illustration of a heat balance model that can be used to calculate absolute core body temperature from a hearing device or other in-ear temperature sensor. More particularly, FIG. 17 shows a heat balance model for both an ITE device and a CIC device, each of which includes a temperature sensor positioned at site 2 of the device for measuring temperature T2 at Location 2 of the ear canal. In FIG. 17, the innermost temperature sensor is positioned to measure temperature $T_2$ at Location 2 and the outermost temperature sensor is positioned to measure temperature $T_1$ ($T_{faceplate}$) at a location more exterior than the innermost temperature sensor (e.g., at the faceplate of the device).

As discussed previously, the best X-Y (surface) location of the shell for a temperature sensor interfaced to the ear is Location 2. The tip is also a good location, but it is not on the shell surface for a hearing device and is typically used to house a receiver. Placing a second sensor at the faceplate provides for measurement of the gradient across the ear shell. This allows calculation of absolute core body temperature using temperature data acquired from only two temperature sensors, although more than two temperature sensors can be used. Closing (occluding) the faceplate by sealing the battery door or using a faceplate with no opening allows the system to compensate for a range of environmental temperatures and draft (wind) conditions. As also noted above, the temperature sensors can be placed under, in or through the shell/faceplate. The temperature sensor can be insulated from the shell, thermally connected to the skin using a high thermal conductivity material or mounted to other substrates with varying thermal properties. The materials interface system can alter the sensitivity and accuracy of the temperature sensors and the total gradient across the shell in order to enhance (e.g., optimize) the system for the application with which it is being used. The temperature sensors can be thermally insulated from the air inside the ear device or from radiant heat coming into the ear device in order to alter the gradient across the shell to meet the needs of a specific application.

Various means of modifying the interface between the temperature sensor and shell and/or between temperature sensor and human have been noted herein (e.g., temperature sensor measurement through the shell, in the shell, under the shell; including of thermally conducting or insulating materials either between the sensor and shell or between the sensor and human, etc.). The effects of these modifications may include making the sensing site of key Location 2 more sensitive to skin temperature change, making the faceplate more or less sensitive to ambient temperature change or draft, and altering the temperature gradient between the sensing site of key Location 2 and the faceplate.

Figure 18:
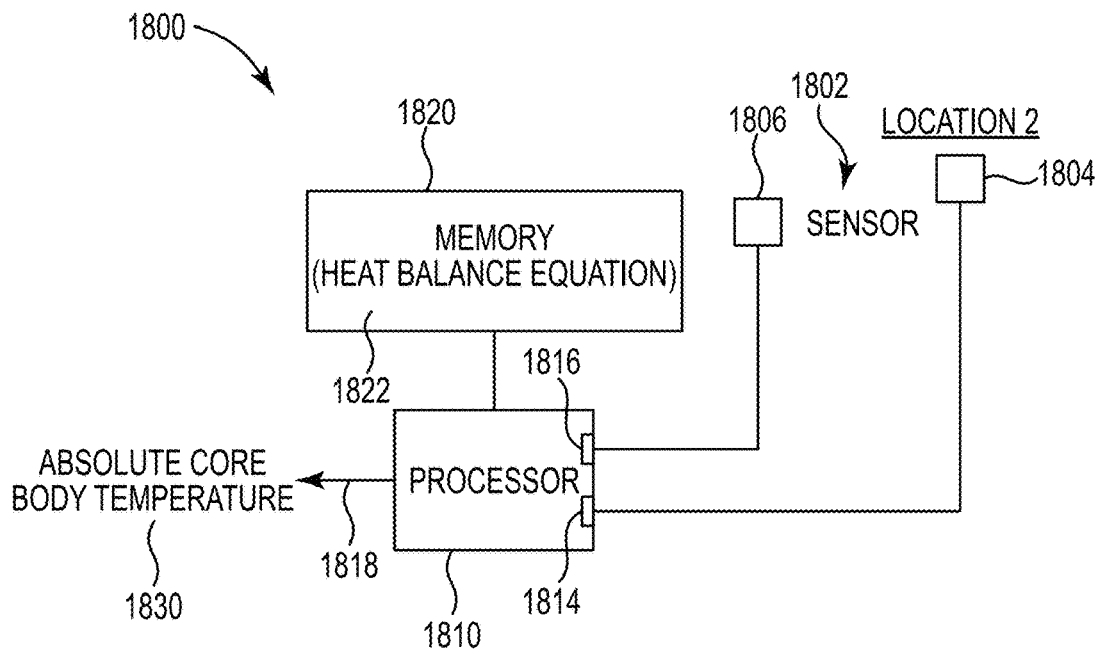
FIG. 18 illustrates a system configured to measure temperature from within an ear canal and to calculate absolute core body temperature in accordance with various embodiments.

FIG. 18 illustrates a system 1800 configured to measure temperature from within an ear canal and to calculate absolute core body temperature in accordance with various embodiments. The system 1800 includes a sensor 1802 which, in the embodiment shown in FIG. 18, includes a distal temperature sensor 1804 and a proximal temperature sensor 1806. The distal temperature sensor 1804 is configured to be located within the ear canal at or near Location 2, described hereinabove as the tragus-side of the ear canal between the first and second bends. The proximal temperature sensor 1806 is configured to be positioned at a location spaced apart from a surface of the ear canal and proximal to the distal temperature sensor 1804 in an outer ear direction. In some configurations, the proximal temperature sensor 1806 is configured to be positioned within the outer ear (e.g., within the ear canal). In other configurations, the proximal temperature sensor 1806 is configured to be positioned exterior of the outer ear.

The system 1800 includes a processor 1810 coupled to a memory 1820. The processor 1810 includes a first ADC 1814 coupled to the proximal temperature sensor 1804, and a second ADC 1816 coupled to the proximal temperature sensor 1806. In some embodiments, the first and second ADC's 1814, 1816, can be functional elements of a separate component which is coupled to respective inputs of the processor 1810. The memory 1820 is configured to store a heat balance equation 1822 developed for the system 1800 in a manner described herein. The processor 1810 is configured to calculate an absolute core body temperature 1830 using the heat balance equation 1822 and temperature signals produced by the distal and proximal temperature sensors 1804, 1806.

A signal indicative of the absolute core body temperature 1830 is provided at an output 1818 of the processor 1810. The processor 1810 may be configured to generate one or more alerts based on a comparison between temperature measurements and one or more thresholds. For example, the processor 1810 can be configured to compute the following temperature measurements: absolute core body temperature continuously; 2) an increase in core body temperature over baseline at any given time of day; 3) a magnitude of variation in core body temperature over any specified time interval within or up to one day (diurnal, nocturnal); and 4) phase shifted daily circadian rhythm compared to normal. A threshold can be established for these and other temperature measurements computed by the processor 1810. The processor 1810 can be a multi-core processor, a digital signal processor (DSP) or a processor incorporating a DSP, a DSP or processor incorporating or coupled to an audio process, and ASIC, or a digital logic device, for example. The memory can be Flash, ferroelectric RAM (FRAM), magnetoresistive RAM (MRAM), and other types of non-volatile memory, for example. The processor 1810 can also incorporate or be coupled to volatile memory, such as RAM.

The processor 1810 can communicate temperature measurements and related alerts in various ways (e.g., via a wireless or wired communication link). In the case of an ear-worn system 1800, for example, temperature readings and related alerts can be communicated to the user through audio messages, if there is no wireless data communication channel present in the system 1800. Temperature readings and related alerts can be transferred to a computer or other device through a base station when recharging or changing batteries of the ear-worn system 1800. The system 1800 may include Bluetooth® and/or other wireless radios (e.g., IEEE 802.11 compliant radios) for communicating with external devices.

According to various embodiments, the temperature sensors 1804, 1806 are implemented as thermistors, such as those previously described. Obtaining accurate temperature measurements using thermistors mounted in or on an ear-worn device can be a challenge. The algorithms developed previously can only produce estimates as accurate as the input data. To achieve high accuracy in resistance measurements, there are two main drivers of inaccuracies: reference accuracy, and analog-to-digital conversion accuracy. By using the Steinhart-hart equation, it is found that reference resistors with tolerances at or below 0.1% will be responsible for an error of 0.05° C. or less when used in conjunction with typical 10 kΩ NTC thermistors measuring typical human body temperatures.

In combination with the reference resistor, there are many ways (Wheatstone bridge, voltage divider, etc.) to measure the resistance of the NTC thermistor and each has its own associated errors depending on circuit layout and environmental noise. In addition to this error, the ADC introduces quantization and other errors. Depending on the chosen resistance measurement technique, a 12 bit ADC should produce a total error of <0.05° C. given that the ADC is accurate to ±1 Least Significant Bit (LSB). Thermistors may have more inaccuracies due to the measurement technique causing self-heating and thus reading resistance that is slightly higher than expected. To avoid heating the thermistors during measurement, it may be desirable to disconnect the temperature sensor circuit while not performing a measurement and keeping the measurement time as short as possible. If disconnecting the circuit is not possible, then using larger reference resistors to limit the amount of power dissipated in the thermistor is also useful, but decreases the resolution of the ADC measurement. The requirements of an accurate measurement are possible to achieve in relatively low cost and small electrical packages making thermistors suitable for in-ear temperature measurements.

Figure 19:
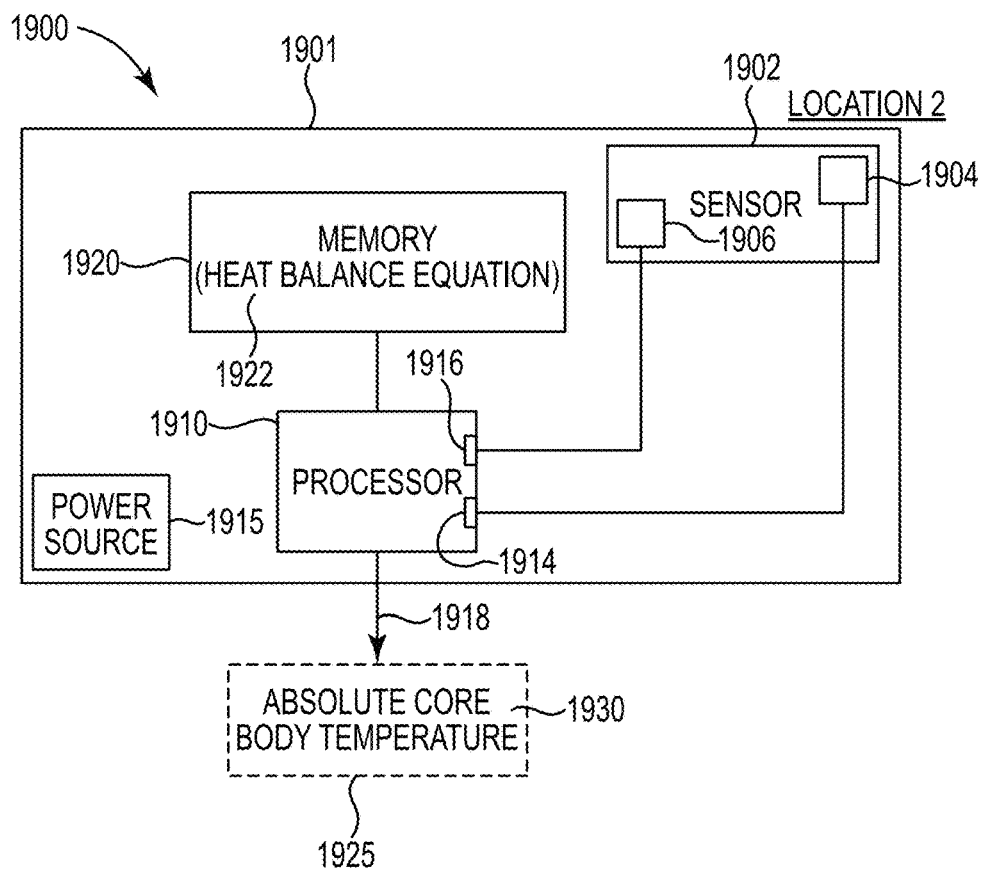
FIG. 19 illustrates a system configured to measure temperature from within an ear canal and to calculate absolute core body temperature in accordance with various embodiments.

FIG. 19 illustrates a system 1900 configured to measure temperature from within an ear canal and to calculate absolute core body temperature in accordance with various embodiments. The system 1900 includes an enclosure or shell 1901 configured for insertion into the ear canal. A distal end of the enclosure 1901 is configured to extend at least beyond the first bend. For example, the system 1900 may be implemented as an ITE, ITC, CIC or IIC device. The system 1900 includes a sensor 1902 which, in the embodiment shown in FIG. 19, includes a distal temperature sensor 1904 and a proximal temperature sensor 1906. The distal temperature sensor 1904 is situated at a location of the enclosure 1901 that faces Location 2 of the ear canal when the enclosure 1901 is fully inserted into the ear canal. The proximal temperature sensor 1906 is situated on the enclosure 1901 at a location spaced apart from the ear canal surface and proximal of the distal temperature sensor in an outer ear direction. For example, the proximal temperature sensor 1906 is configured to be positioned within the outer ear (e.g., interior or exterior of the aperture of the ear canal), such as on a faceplate of the enclosure 1901.

The system 1900 includes a processor 1910 coupled to a memory 1920. The processor 1910 includes a first ADC 1914 coupled to the proximal temperature sensor 1904, and a second ADC 1916 coupled to the proximal temperature sensor 1906. The processor 1910 is configured to calculate an absolute core body temperature 1930 using temperature signals produced by the distal and proximal temperature sensors 1804, 1806 and a heat balance equation 1922 stored in the memory 1920. Temperature measurements and alerts, such as those described above, can be communicated to the user and/or other devices via the output 1918 of the processor 1910. For example, temperature measurements, alerts, physiologic, and diagnostic information generated by the processor 1910 can be presented on a display 1925 of a device (e.g., smartphone) communicatively coupled to the system 1900 via a wireless communication link (e.g., Bluetooth® or IEEE 802.11 compliant link). The system 1900 also includes a power source 1915, such as a rechargeable or conventional battery.

Figure 20:
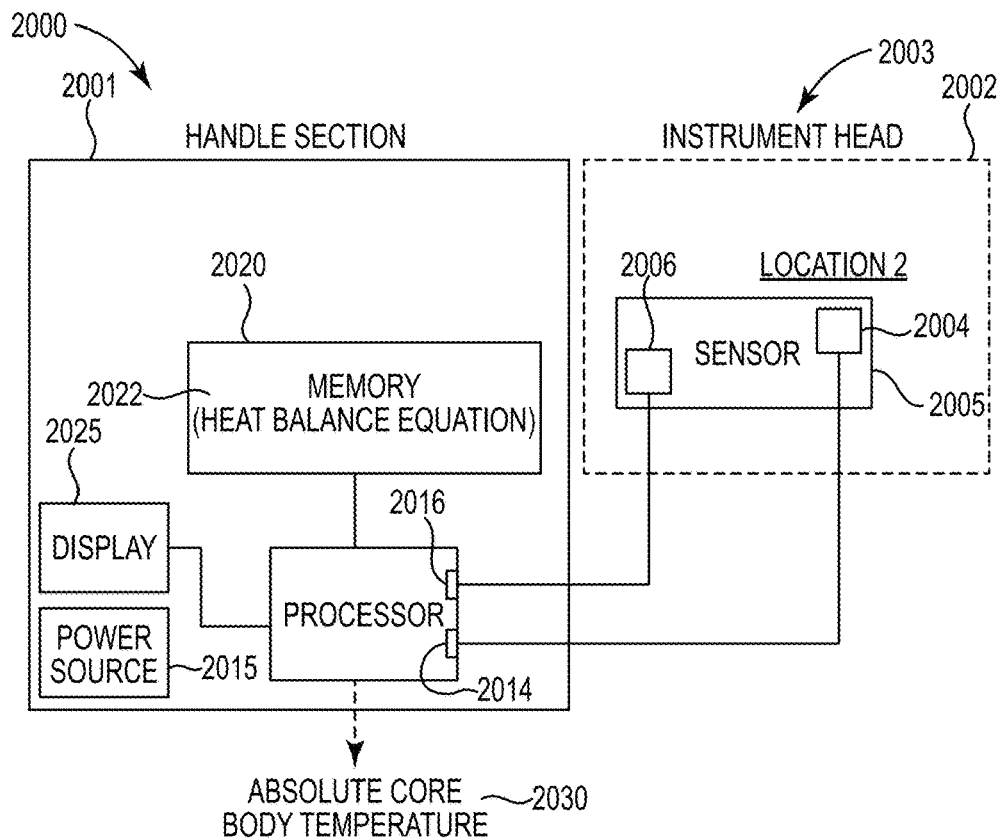
FIG. 20 illustrates a system configured to measure temperature from within an ear canal and to calculate absolute core body temperature in accordance with various embodiments.

FIG. 20 illustrates a system 2000 configured to measure temperature from within an ear canal and to calculate absolute core body temperature in accordance with various embodiments. The system 2000 includes a handle section 2001 and an instrument head 2003 coupled to the handle section 2001. In some configurations, the instrument head 2003 is mechanically coupled to the handle section 2001. In other configurations, the instrument head 2003 is a separate structure which can be inserted into the ear canal and communicatively couples to the handle section 2001 via a wired or wireless communication link.

The handle section 2001 is configured as a hand-graspable section of the system 2000. The instrument head 2003 includes an enclosure or shell 2002 configured for insertion into the ear canal. A distal end of the enclosure 2002 is configured to extend at least beyond the first bend. In the embodiment shown in FIG. 20, the instrument head 2003 supports a sensor 2005 comprising a distal temperature sensor 2004 and a proximal temperature sensor 2006. The distal temperature sensor 2004 is situated at a location of the enclosure 2002 that faces Location 2 of the ear canal when the enclosure 2002 is fully inserted into the ear canal. The proximal temperature sensor 2006 is situated on the enclosure 2002 at a location spaced apart from the ear canal surface and proximal of the distal temperature sensor 2004 in an outer ear direction. For example, the proximal temperature sensor 2006 is configured to be positioned within the outer ear (e.g., interior or exterior of the aperture of the ear canal) when the enclosure 2002 is fully inserted into the ear canal.

The handle section 2001 houses a processor 2010 coupled to a memory 2020 and a display 2025 (e.g., LED, LCD, OLED, e-ink). The processor 2010 includes a first ADC 2014 coupled to the proximal temperature sensor 2004, and a second ADC 2016 coupled to the proximal temperature sensor 2006. The processor 2010 is configured to calculate an absolute core body temperature 2030 using temperature signals produced by the distal and proximal temperature sensors 2004, 2006 and a heat balance equation 2022 stored in the memory 2020. Temperature measurements, alerts, physiologic, and diagnostic information generated by the processor 2010 can be presented on the display 2025 (e.g., a touch screen) of the handle section 2001. This information can also be communicated to other devices via the output 2018 of the processor 2010 (via a wired or wireless communication interface). The system 2000 also includes a power source 2015, such as a rechargeable or conventional battery.

Figure 21:
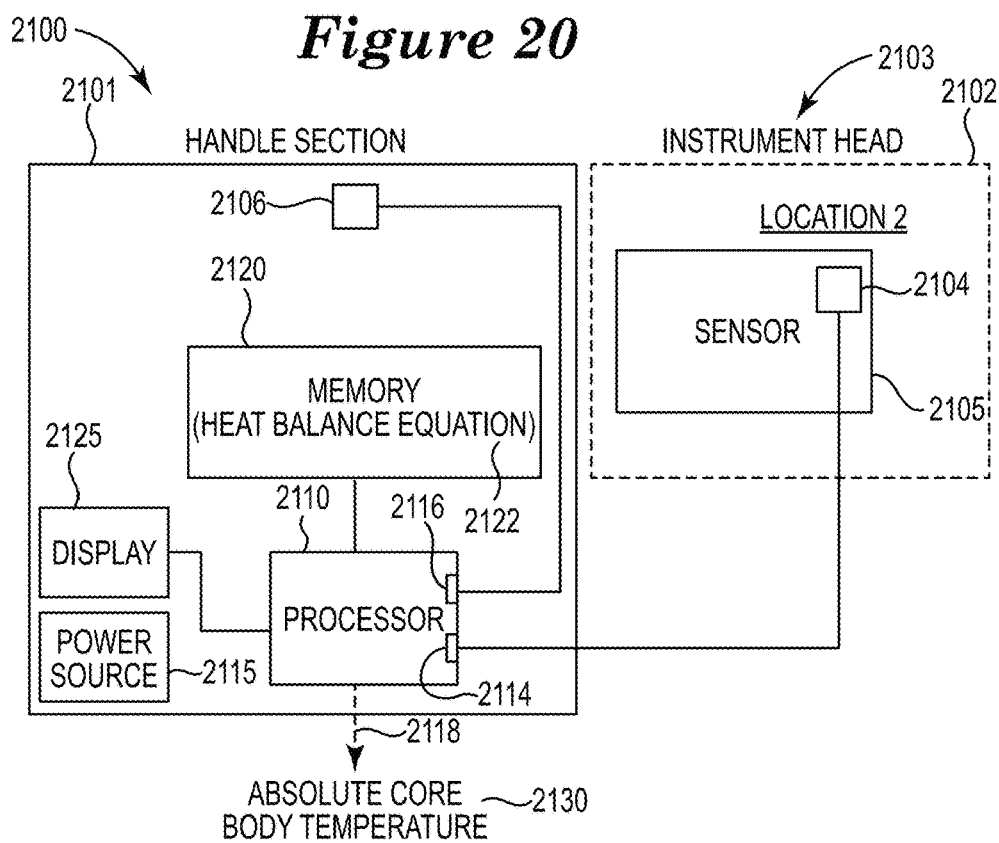
FIG. 21 illustrates a system configured to measure temperature from within an ear canal and to calculate absolute core body temperature in accordance with various embodiments.

FIG. 21 illustrates a system 2100 configured to measure temperature from within an ear canal and to calculate absolute core body temperature in accordance with various embodiments. The system 2100 includes a handle section 2101 and an instrument head 2103 coupled to the handle section 2101. In some configurations, the instrument head 2103 is mechanically coupled to the handle section 2101. In other configurations, the instrument head 2103 is a separate structure which can be inserted into the ear canal and communicatively couples to the handle section 2101 via a wired or wireless communication link.

The handle section 2101 is configured as a hand-graspable section of the system 2100. The instrument head 2103 includes an enclosure or shell 2102 configured for insertion into the ear canal. A distal end of the enclosure 2102 is configured to extend at least beyond the first bend. In the embodiment shown in FIG. 21, the instrument head 2103 supports a sensor 2105 comprising a distal temperature sensor 2104. The distal temperature sensor 2104 is situated at a location of the enclosure 2102 that faces Location 2 of the ear canal when the enclosure 2102 is fully inserted into the ear canal. A proximal temperature sensor 2106 is situated on or in the enclosure of the handle section 2101, and is configured to produce a temperature signal indicative of the ambient environment exterior of the ear. In the embodiment shown in FIG. 21, the proximal temperature sensor 2106 is preferably a temperature sensor configured to sense conductive and/or convective heat, rather than radiative heat (e.g., a thermistor, RTD, or thermocouple rather than an IR sensor).

The handle section 2101 houses a processor 2110 coupled to a memory 2120 and a display 2125 of a type described above. The processor 2110 includes a first ADC 2114 coupled to the proximal temperature sensor 2104, and a second ADC 2116 coupled to the proximal temperature sensor 2106. The processor 2110 is configured to calculate an absolute core body temperature 2130 using temperature signals produced by the distal and proximal temperature sensors 2104, 2106 and a heat balance equation 2122 stored in the memory 2120. Temperature measurements, alerts, physiologic, and diagnostic information generated by the processor 2110 can be presented on the display 2125 of the handle section 2101. This information can also be communicated to other devices via the output 2118 of the processor 2110 (via a wired or wireless communication interface). The system 2100 also includes a power source 2115, such as a rechargeable or conventional battery.

Figure 22:
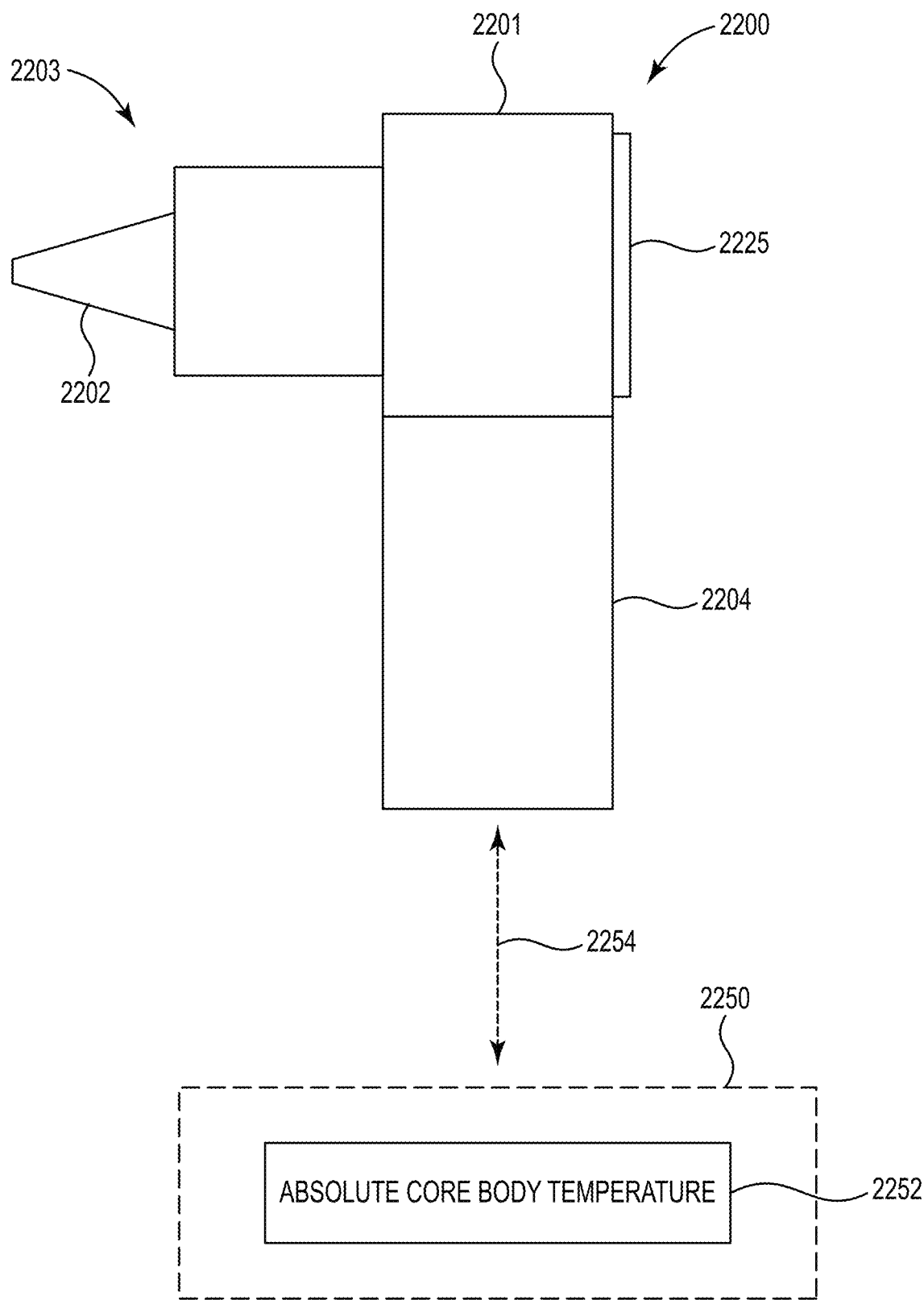
FIG. 22 illustrates a system configured to measure temperature from within an ear canal and to calculate absolute core body temperature in accordance with various embodiments.

FIG. 22 illustrates a system 2200 configured to measure temperature from within an ear canal and to calculate absolute core body temperature in accordance with various embodiments. The system 2200 includes a handle section 2201 and an instrument head 2203 mechanically coupled to the handle section 2201. The handle section 2201 includes a display 2225 and a hand-graspable section 2204. The instrument head 2203 includes an enclosure or shell 2202 configured for insertion into the ear canal. A distal end of the enclosure 2202 is configured to extend at least beyond the first bend. Although shown as having a frustoconical shape, the enclosure 2202 can deform during insertion into the ear canal to extend at least beyond the first bend. In some configurations, the distal end of the enclosure 2202 is shaped to facilitate easy insertion past the first bend. The handle section 2201 and instrument head 2203 are configured to accommodate the circuitry and provide the functionality described previously with reference to FIGS. 20 and 21.

In some embodiments, the system 2200 is configured to communicate with a separate device or system 2250 via a wired or wireless communication link 2254. The device 2250 can be a smartphone, laptop, tablet, or phablet, for example. The device 2250 includes a display 2252 configured to present temperature measurements, alerts, physiologic, and diagnostic information generated by the system 2200.

Figure 23:
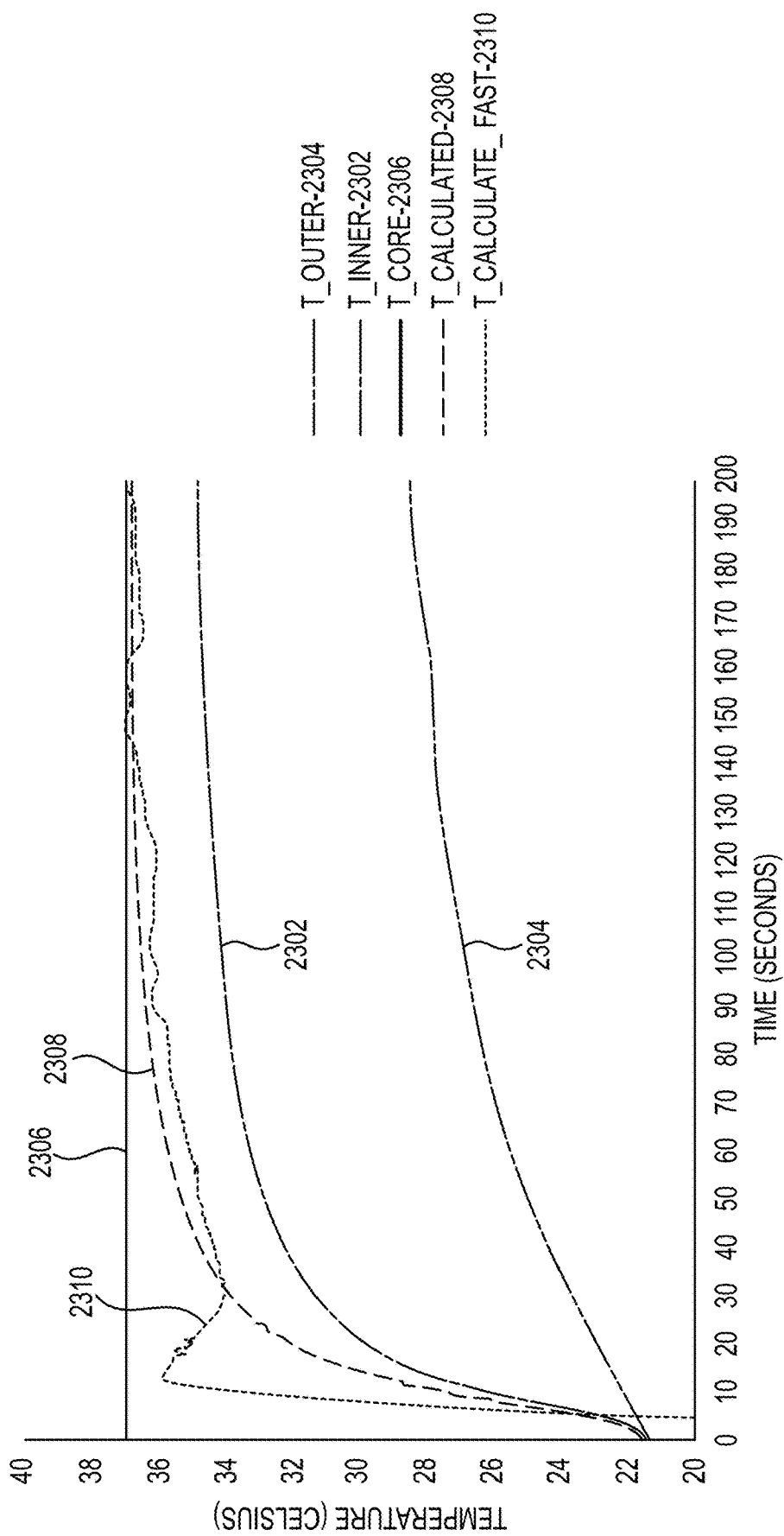
FIG. 23 is a graph showing several temperature curves that can be measured and/or calculated by a hand-graspable thermometer or an in-ear device to provide a fast estimation of a final in-ear temperature in accordance with various embodiments.

In some embodiments, such as a hand-graspable thermometer shown in FIGS. 20-22, it may be desirable to obtain a fast temperature measurement that estimates the final temperature soon after inserting the temperature sensing device into the ear. Reference is made to FIG. 23, which shows several temperature curves that can be measured and/or calculated by a hand-graspable thermometer (or an in-ear device). Curve 2302 (T_inner) shows temperature measured by a distal thermistor (e.g., situated to measure in-ear temperature at Location 2). Curve 2304 (T_outer) shows temperature measured by a proximal thermistor (e.g., situated proximal of the distal thermistor). Curve 2306 (T_core) shows core temperature measured by a reference thermometer, which is used in the heat balance equation as $T_{oral}$. Curve 2308 (T_calculated) is temperature computed directly using the heat balance equation and temperatures from the distal and proximal thermistors.

Curve 2310 (T_calculate_fast) is a combination of estimated temperature (computed within an initial time period) followed by a calculated temperature (computed subsequent to the initial time period). When the temperature sensing device is first inserted into the ear, the distal and proximal thermistor temperatures start to rise rapidly, followed by a gradual rise thereafter until a final temperature is reached. During the initial time period (e.g., at times below about 10 sec), an estimate of the final temperature is computed using the slopes of curves 2302 and 2304. After the initial time period, the slopes of curves 2302 and 2304 decrease (e.g., after about 30 sec), and the final temperature is computed using the heat balance equation and temperatures from the distal and proximal thermistors. This approach provides a more accurate temperature measurement initially, followed by high accuracy subsequently because the final temperature is computed using the above-described heat balance equation approach.

It is understood that various embodiments described herein may be implemented with any ear-worn electronic device without departing from the scope of this disclosure. The devices depicted in the figures are intended to demonstrate the subject matter, but not in a limited, exhaustive, or exclusive sense. Ear-worn electronic devices, such as hearables (e.g., wearable earphones and earbuds), hearing aids, and hearing assistance devices, typically include an enclosure, such as a housing or shell, within which internal components are disposed. Typical components of an ear-worn electronic device can include a digital signal processor (DSP), memory, power management circuitry, one or more communication devices (e.g., a radio, a near-field magnetic induction (NFMI) device), one or more antennas, one or more microphones, and a receiver/speaker, for example. Some ear-worn electronic devices can incorporate a long-range communication device, such as a Bluetooth® transceiver or other type of radio frequency (RF) transceiver. A communication device (e.g., a radio or NFMI device) of an ear-worn electronic device can be configured to facilitate communication between a left ear device and a right ear device of the ear-worn electronic device.

Ear-worn electronic devices of the present disclosure can incorporate an antenna arrangement coupled to a high-frequency radio, such as a 2.4 GHz radio. The radio can conform to an IEEE 802.11 (e.g., WiFi®) or Bluetooth® (e.g., BLE, Bluetooth® 4.2 or 5.0) specification, for example. It is understood that hearing devices of the present disclosure can employ other radios, such as a 900 MHz radio. Ear-worn electronic devices of the present disclosure can be configured to receive streaming audio (e.g., digital audio data or files) from an electronic or digital source. Representative electronic/digital sources (e.g., accessory devices) include an assistive listening system, a TV streamer, a radio, a smartphone, a laptop, a cell phone/entertainment device (CPED) or other electronic device that serves as a source of digital audio data or other types of data files. Ear-worn electronic devices of the present disclosure can be configured to effect bi-directional communication (e.g., wireless communication) of data with an external source, such as a remote server via the Internet or other communication infrastructure.

The term ear-worn electronic device of the present disclosure refers to a wide variety of ear-level electronic devices that can aid a person with impaired hearing. The term ear-worn electronic device also refers to a wide variety of devices that can produce optimized or processed sound for persons with normal hearing. Ear-worn electronic devices of the present disclosure include hearables (e.g., earbuds) and hearing aids (e.g., hearing instruments), for example. Ear-worn electronic devices include, but are not limited to ITE, ITC, CIC or IIC type hearing devices or some combination of the above. In this disclosure, reference is made to an "ear-worn electronic device," which is understood to refer to a system comprising a single ear device (left or right) or both a left ear device and a right ear device.

Figure 24:
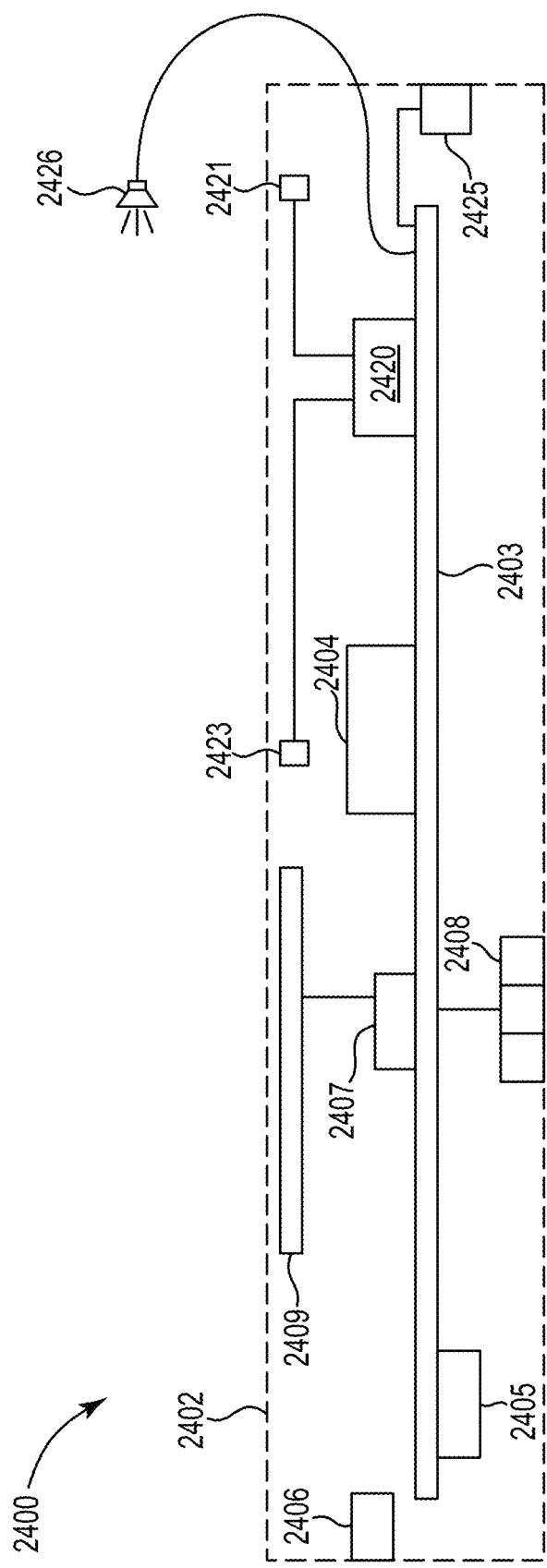
FIG. 24 is a block diagram showing an ear-worn electronic device that can be configured to incorporate a temperature sensor arrangement of a type described herein in accordance with various embodiments.

FIG. 24 is a block diagram showing various components of an ear-worn electronic device 2400 that can be configured to incorporate a temperature sensor arrangement of a type previously described in accordance with various embodiments. For example, the block diagram of FIG. 24 shows an ear-worn electronic device 2400 that can incorporate the embodiments shown in FIGS. 18 and 19 and implement the functionality illustrated in FIG. 2. It is understood that an ear-worn electronic device 2400 may exclude some of the components shown in FIG. 24 and/or include additional components. It is also understood that the ear-worn electronic device 2400 illustrated in FIG. 24 can be either a right ear-worn device or a left-ear-worn device. The components of the right and left ear-worn devices can be the same or different.

The ear-worn electronic device 2400 shown in FIG. 24 includes an enclosure 2402 within which several components are electrically connected to a mother flexible circuit 2403. A battery 2405 is electrically connected to the mother flexible circuit 2403 and provides power to the various components of the ear-worn electronic device 2400. One or more microphones 2406 are electrically connected to the mother flexible circuit 2403, which provides electrical communication between the microphones 2406 and a DSP 2404. Among other components, the DSP 2404 can incorporate or be coupled to audio signal processing circuitry. One or more user switches 2408 (e.g., on/off, volume, mic directional settings, mode selection) are electrically coupled to the DSP 2404 via the flexible mother circuit 2403.

A sensor 2420 is coupled to the DSP 2404 or other processor of the device 2400 via the mother flexible circuit 2403. The sensor 2420 is coupled to a distal temperature sensor 2421 and a proximal temperature sensor 2423. The distal temperature sensor 2421 is situated at a location of the enclosure 2402 that faces Location 2 of the ear canal when the enclosure 2402 is fully inserted into the ear canal. The proximal temperature sensor 2423 is situated on the enclosure 2402 at a location spaced apart from the ear canal surface and proximal of the distal temperature sensor 2421 in an outer ear direction. The DSP 2404, or other processor or logic circuitry coupled to the sensor 2420, is configured to calculate an absolute core body temperature using the first and second temperatures measured by the distal and proximal temperatures sensors 2421, 2423 and a heat balance equation stored in a memory of, or coupled to, the DSP 2404 or other processor/logic circuitry.

In some embodiments, the DSP 2404 has an audio output stage coupled to a speaker 2425. In other embodiments, the audio output stage of the DSP 2404 is coupled to a receiver 2426. It is noted that the distal temperature sensor 2421 can be mounted on the receiver 2426 at a position that can measure temperature at or near Location 2 of the ear canal. The proximal temperature sensor 2423 can also be mounted on the receiver 2426 at a location more exterior than the distal temperature sensor 2421 (e.g., in an outer ear direction). Alternatively, the proximal temperature sensor 2423 can be mounted in or on the enclosure 2402. In an optional sensor arrangement 2420, one or more sensors (e.g., ECG, EEG, EOG, IMU, accelerometer, gyroscope, magnetometer) can be coupled to the DSP 2404 via the mother flexible circuit 2403.

The ear-worn electronic device 2400 may incorporate a communication device 2407 coupled to the flexible mother circuit 2403 and to an antenna 2409. The communication device 2407 can be a Bluetooth® transceiver, such as a BLE (Bluetooth® low energy) transceiver or other transceiver (e.g., an IEEE 802.11 compliant device). The communication device 2407 can be configured to communicate with an external device, such as a smartphone or laptop, in accordance with various embodiments.

EXAMPLE

The following example, which describes various experiments conducted by the inventors, is merely for illustrative purposes only and is not meant to be limiting on the scope of the appended claims.

Data Acquisition System

All experiments were run using an Omega OM-USB-TEMP data logger with 8 channels at 2 Hz sampling frequency. The data logger uses the Steinhart-Hart equation to convert resistance to temperature using the Steinhart-Hart constants. The data logger was turned on 30 minutes prior to calibration and temperature measurements per the manufacturer's recommendations. The mean temperature over a 2-minute duration (sample size=240) was reported as the temperature value for each experimental run.

Thermistors Calibration Set-Up

Thermistors were tested over the environmental temperature range of 35.8° C. to 42° C. per ASTM E1112 (Standard Specification for Electronic Thermometer for Intermittent Determination of Patient Temperature) using 1-hour equilibration times per test. Tests were also conducted in air using a calibrated Test Equity Half-Cube Temperature Chamber (Model 105, Thousand Oaks, Calif.) oven as a more practical method for incoming component or manufactured product testing procedures.

Eight thermistors per supplier were tested in a draft-free stainless steel container at 24, 34, 35.8, 37, 38, 41 and 42° C.

A Tegam Model 840 temperature acquisition system with +/−0.2° C. repeatability and 0.1° C. resolution was used with a K-type GK11M thermocouple for measuring air temperature. The mean difference (between the measured value and the reference probe) and the 95% confidence intervals (CI) for the thermistors were calculated at each of the 7 temperature settings.

Thermistors

Negative temperature coefficient (NTC) thermistors with a nominal 10 K-ohm resistance from Ametherm (Part #DG103395) with an unspecified error or Murata (Part #NTH-C125-18XH103) with a specified error of +/−0.1° C. over the temperature range of interest were used in all experiments. Experiments showed no significant differences in bias across the temperature range of 24 to 42° C. for both thermistors. The average mean bias and 95% CI was found to be 0.3311 (+/−0.1955) and 0.1569 (+/−0.0454) (DF=7, t=2.365) for 8 Ametherm and Murata thermistors respectively. The reference probe error partially contributed to the inaccuracies measured however, the precision of the Ametherm thermistor was insufficient and a "control" sensor was mounted to the tip of a hearing aid shell and placed in a draft free enclosure at room temperature during all experiments to correct for the bias from thermistor-to-thermistor. Each thermistor bias was then calculated as the average of the thermistor temperature minus the average value for the control. This technique allowed the best method for matching the sensors by not adding the variability from an external reference tool.

All experiments using the newly available high precision Murata thermistor were done with no bias correction.

Teflon-coated 36 AWG 2½ foot wire extensions composed of 7 strands of 44 AWG (36⁷⁄₄₄) were soldered to the terminals of the thermistors. The thermistors were then attached to the shells or other intermediate structures using Dynmax 9422-SC ultra-violet (UV) curable adhesive or Loctite 401 (P/N 34846) and the end wires were directly connected to the data logger.

Hearing Device Shell

Methacrylate in-the-ear (ITE) custom fit shells were manufactured using stereo-lithography (SLA) by first scanning a negative mold impression of the ear and the ear-canal then using standard procedures for 3-dimensional modeling of the device. Shells were formed with a sound bore hole at the tip, with and without a standard size vent commonly used in hearing products.

Faceplates 2 mm thick cellulose acetate propionate (Eastman™) faceplates with a battery door were attached onto the ITE shells using Loctite 406 Instant adhesive (P/N 31664). The thermistor leads were run through the battery door and the door was sealed with Room-Temperature-Vulcanization (Momentive RTV118) silicone to prevent a draft. Thermistors were mounted on the faceplate using Dynmax 9422-SC UV curable adhesive or Loctite 401 (P/N 34846) or interfaced to intermediate structures and then attached.

Human Temperature Reference Tools

An FDA approved Covidien Genius II clinical grade handheld infrared thermometer was used to obtain reference temperatures from the tympanic membrane. A full Gage Repeatability and Reproducibility experiment was performed using multiple operators and multiple subjects and the tool was found to be limited by high variability. This was thought to be due to the inability to repeatedly hit the targeted tympanic membrane when taking the readings. It was compensated for by taking 5 readings, discarding the lowest 2 and averaging the remaining 3 for each experimental run.

An FDA approved Gear District thermometer with +/−0.1° C. error made by Hangzhou Sejoy Electronics and Instruments Co. (Hangzhou, China) was used as the oral thermometry reference. The thermometer was moderately sensitive to environmental temperature. This was not corrected for in all experiments done with the DG103395 thermistors but was largely corrected by equilibrating the thermometer in the mouth for 20 minutes prior to the first reading and minimizing the time the thermometer was out of the mouth during subsequent readings for the experiments done with the Murata thermistors in the shell.

An Exergen TAT-2000C SmartGlow temporal scanner was used for measurements from the forehead. The device is FDA approved and has an unspecified error. Readings from the thermometer were very sensitive to draft. This may be due to draft cooling the environmental temperature sensor in the handheld device or the forehead and no effort was made to correct for this.

Study 1. Gradient Across the Ear

Subjects were one middle aged female and one middle aged male. No health screening or exclusions of normal living was considered. Experiments were run between noon and 1 pm at room temperature in an office environment.

Study 2. Re-insertion of the Ear Shell

Subjects were 1 female and 4 males with an age range of 20 to 60. No health screening or exclusions of normal living was considered. All experiments were run in an office environment between the hours of 1 pm and 5 pm on different days.

Study 3. Thermistor-to-Ear Interfaces Under Blocked Ambient Conditions

Subjects were 1 female and 4 males with an age range of 20 to 60. No health screening or exclusions of normal living was considered. All experiments were run in an office environment between the hours of 1 pm and 5 pm on different days. In order to block the effect of uncontrolled room temperature each subject was measured once until all subjects were measured and then the sequence was repeated 3 times with the subjects re-inserting the ear shell and allowing it to equilibrate 30 minutes in between experimental runs.

Study 4. Predicting Body Temperature in a Range of Environmental Temperatures and Draft in an ITE Shell Four persons, 1 female and 3 males with an age range of 29 to 60 were tested over an ambient temperature range of 5 to 32° C. Five-degree temperature readings were taken from a walk-in refrigeration unit with the subjects standing. Room temperature readings were taken in an office environment with the subjects sitting. High temperature readings were taken inside a heated walk-in chamber. Draft was delivered by a fan powered by an Invertek Drive (TP66) (McIntosh and Bhunia, 2015). Wind speed was set at 5 mph at face level using a hot wire anemometer (Fischer Scientific). Two sets of experiments were run using the DG103395 Ametherm thermistors in ITE shells in one set of experiments and the Murata high precision thermistors under the ITE shell in another.

Study 5. Modifying the Gradient Across the Ear Shell

Air, foam, and silicone were used as fill material in an ITE shell (with thermistors at Location 2 and the faceplate) in order to evaluate the effect on the temperature gradient across the shell. Tests were done at 15, 22 and 31° C. and a wind test at 5 mph was done at the room temperature condition for each materials system on one subject. Room-Temperature-Vulcanization (Momentive RTV118) silicone and MLC Closed cell foam (Seattle Fabrics Inc., Seattle, USA) were used as fill materials.

Study 6. Obtaining Accurate Body Temperature in a Range of Environmental Temperatures and Draft Using Thermistors Near the Receiver/Speaker of a Standard Earbud Hearing Device Four persons, 1 female and 3 males with an age range of 29 to 60 were tested over an ambient temperature range of 4 to 32° C. Low temperature readings were taken outdoors or a walk-in refrigerator with the seated subjects. Room temperature readings were taken in an office environment with the subjects sitting. High temperature readings were taken inside a heated walk-in chamber. Draft was delivered by a fan powered by an Invertek Drive (TP66) (McIntosh and Bhunia, 2015). Wind speed was set at 5 mph at face level using a hot wire anemometer (Fischer Scientific). All tests were done with the Murata high precision thermistors.

Results

Study 1. The Temperature Gradient Across the Ear

DG103395 thermistors were placed through the shell in each of the 7 locations in the left and right shells in order to evaluate the temperature gradient across the ear as shown in FIGS. 4A and 4B. Locations 1 and 2 are located in the posterior and anterior sides of the ear canal while location 7 is located inside the tragus. Locations 4 and 5 are adjacent to the posterior concha and location 6 is located adjacent to the cymba concha.

Figure 5:
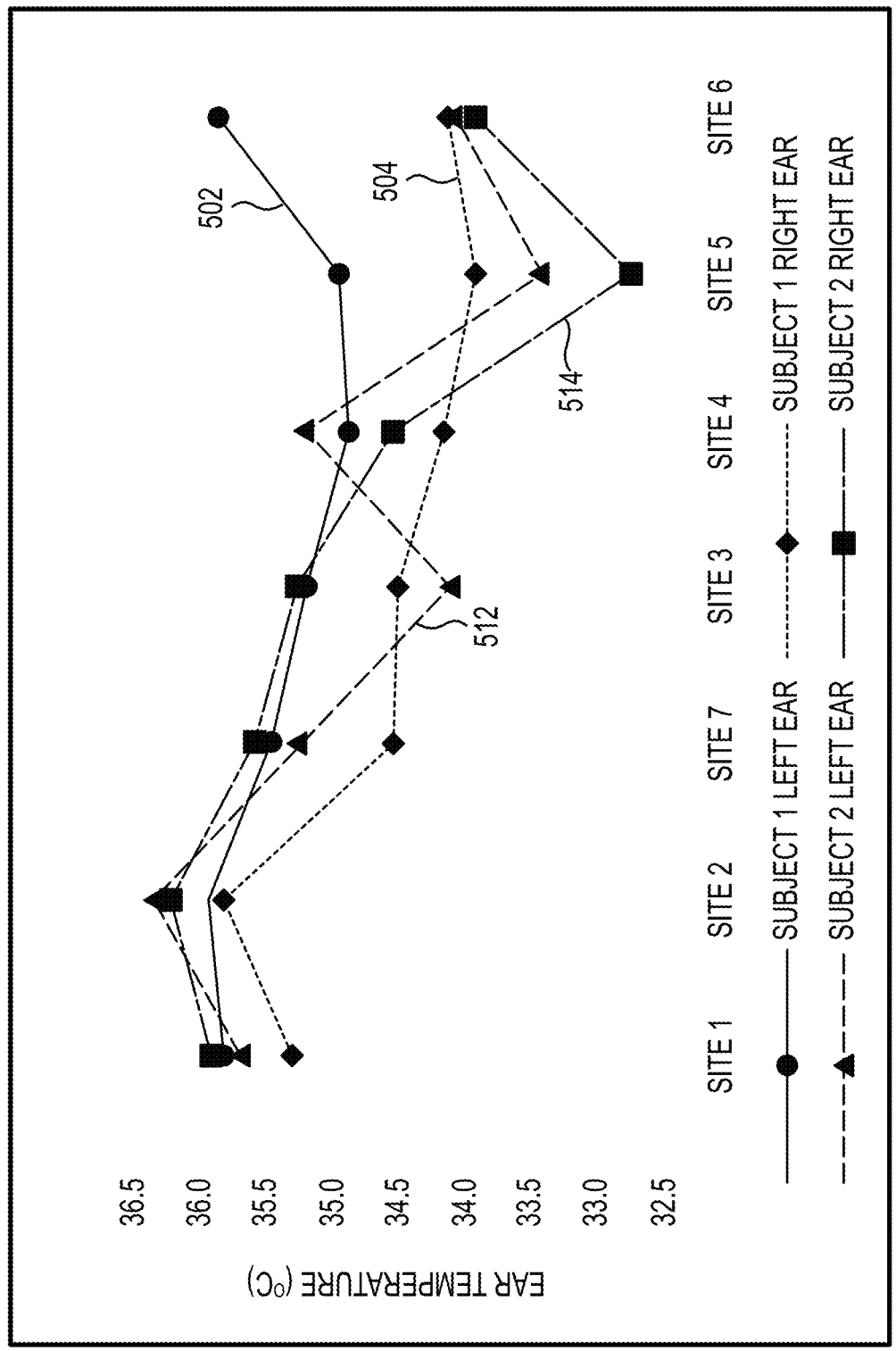
FIG. 5 shows bias-corrected temperature across two experimental ear shells (left and right) measured simultaneously from the ear of each of two subjects.

FIG. 5 shows the bias-corrected temperature across 2 ear shells (left and right) measured simultaneously from the ear of each of the 2 subjects. The temperature of each ear progressively decreased with extension of the ear outwards from the head with the highest temperature located on anterior side of the innermost canal region corresponding to Location 2. Less variability was measured from ear-to-ear at the locations furthest inside the ear canal. Locations 1 and 2 were thus selected for further studies in order to avoid large person-to-person temperature variability at a single thermistor site.

Study 2. Re-Insertion of the Ear Shell

The variation in fit of the hearing aid shell due to insertion into the ear was a concern even for the custom made devices. An assessment was made of the ability to get accurate measurements from multiple reinsertions of a hearing aid shell in 5 persons. To evaluate the difference in local temperature from a reference thermometer, thermistors were attached under the shell at locations 1 and 2 and a third thermistor was placed through the sound bore hole extending just outside the ear shell.

Temporal and oral thermometers were used as reference tools to simultaneously take 5 measurements of temperature during each run. The experiments were run in the afternoon at room temperature on different days for each subject resulting in an ambient temperature range of 22.6 to 24.4° C. The mean temperature difference and standard deviation over all measured values (n=75) for each site were calculated. This experiment demonstrated the best agreement between the tip location and the oral thermometer reference thermometers followed by Location 2 from under the shell and the oral thermometer.

Bland-Altman plots were generated of the mean difference (MD) of the average of the reference tool temperature and the thermistor temperature versus the difference between the reference tool temperature and the thermistor for each location studied. The Bland-Altman plots showed the difference in temperature from the thermistor at Location 2 in the left ear to the temporal and oral reference thermometers. The plots both show a downward trend in the MD of data indicating that comparing the standard deviation from one case to another is confounded by a tendency of the ear temperature and/or the reference thermometer temperature to change relative to ambient temperature. This rendered any attempt to calculate limits-of-agreement invalid using the raw data. This problem was mitigated by running the next set of experiments simultaneously with the subjects at the same room temperature.

Study 3. Thermistor to Ear Interfaces Under Blocked Ambient Conditions

An experiment was run at room temperature using thermistors at locations 1, 2 and the tip of both the left and right in-the-ear (ITE) shell. Five (5) subjects were measured in the same time frame at the same ambient temperature. Tympanic infrared (IR), temporal and oral reference temperatures were taken simultaneously.

Three different thermistor-to-ear interface systems were evaluated in three different experiments. The interface between the thermistor and the ear was modified by embedding the thermistor in the shell or placing it through or under the shell. Thermistors placed through the shell showed the lowest mean difference between the thermistors at Location 2 or the tip and the oral thermometer. Thermistors placed under the shell showed improved precision at Location 2. Based on these results and the ease-of-manufacturing considerations, thermistors placed under the shell at Location 2 and the oral reference probe were selected for further studies.

Study 4. Predicting Body Temperature in a Range of Environmental Temperatures and Draft in an ITE Shell The temperature in the ear canal changes due to environmental temperature and draft and a system was required to compensate for this change. The heat balance method in the ear used by Pompei and Pompei (1996) for an external infrared tympanic thermometer (IR thermometer) was modified by the inventors for the application of measuring temperature from an ITE shell using two permanently fixed thermistors. The Pompei and Pompei apparatus included a temperature sensor in the handle of the IR thermometer and an IR sensor in the ear piece. It was understood by the inventors, however, that the equation derived by Pompei and Pompei is a radiation-based heat balance equation, and does not work when two temperature sensors are placed in the ear. Moreover, while Pompei and Pompei were able to obtain an environmental temperature from the handheld probe with an IR sensor, the radiating effects of the head precluded environmental temperature from being taken from an ear-worn device. In this study, two thermistors (innermost and outermost) were positioned in the ear via the ITE device. In addition to the innermost thermistor (positioned for measuring temperature at Location 2), a second sensor was placed under the faceplate of the ITE device and a new heat balance equation was developed around the thermistor innermost in the ear using a simple heat balance model, details of which are provided below.

Heat Balance Model

One dimensional conductive heat transfer model across a flat plate assumes an infinite plate size in the lateral directions, where the heat flux (q) is calculated using the equation:

$$q=k(T_{inside}-T_{outside})/d \quad (1)$$

where k is the thermal conductivity of the material, d is the thickness of the plate and $T_{inside}$ and $T_{outside}$ are the temperatures on each side of the plate.

Figure 25:
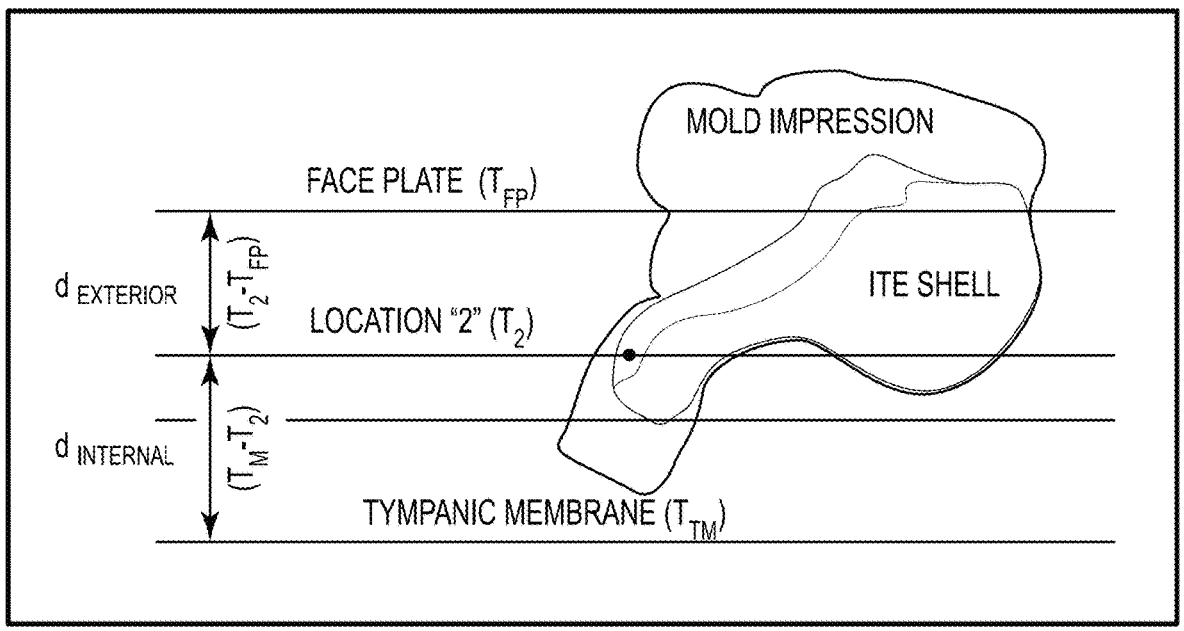
FIG. 25 is an illustration of a heat balance model used to calculate absolute core body temperature for a hearing device in accordance with various embodiments.

For a thermal model of the heat flow through the ITE shell from the inner parts of the ear to the ambient, the ear was taken to be one dimensional with unknown thicknesses and conductivities (see FIG. 25).

This resulted in the two following equations:

$$q_{influx}=K'_{interior}(T_{tympanic\ membrane}-T_{internal})/d_{internal} \quad (2)$$

where $T_{inside}=T_{TM}$ is the temperature at the tympanic membrane, $T_{outside}=T_{internal}$, the temperature from the interior most thermistor in the ear and $d_{internal}$ is approximately the depth of the internal ear from the shell at the location of the innermost thermistor and the tympanic membrane.

$$q_{efflux}=K'_{Exterior}(T_{internal}-T_{faceplate})/d_{exterior} \quad (3)$$

where $T_{inside}-T_{inner}$ (the temperature from the innermost thermistor in the ear), $T_{outside}=T_{faceplate}$ (the temperature from the faceplate) and $d_{exterior}$ is approximately the depth of the external ear shell from the faceplate to the innermost thermistor location.

The K' values are composite thermal transfer coefficients. At equilibrium, $q_{influx}=q_{efflux}$ so that:

$$K'_{Internal}(T_{tympanic\ membrane}-T_{internal})/d_{internal}=K'_{exterior}(T_{internal}-T_{faceplate})/d_{exterior} \quad (4)$$

and, $$T_{internal}-T_{faceplate})/(T_{tympanic\ membrane}-T_{internal})=K'_{internal}d_{exterior}/K'_{Exterior}d_{internal} \quad (5)$$

Theoretically, a plot of $(T_{TM}-T_{int})$ versus $(T_{int}-T_{ext})$, or in the case considered $(T_{oral}-T_{Location\ 2})$ versus $(T_{Location\ 2}-T_{faceplate})$, would then give a consistent value when the ear is at equilibrium with the environment.

Figure 26:
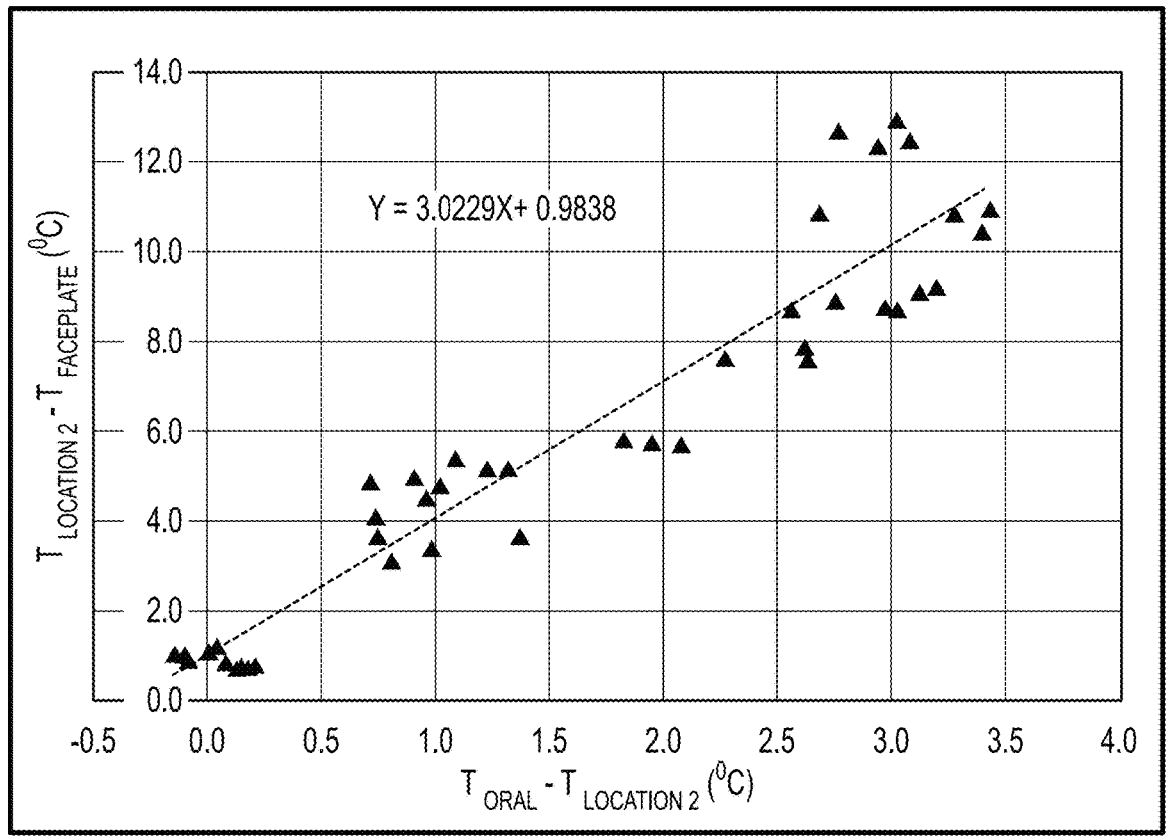
FIG. 26 is a graph illustrating a heat balance equation developed from three persons and derived from temperature measurements taken from a first type of temperature sensors in an ITE shell in accordance with various embodiments.

The concept was tested using DG103395 sensors in an ITE shell at Location 2 and the oral thermometer as the reference probe. Three (3) persons were tested over an ambient temperature range of 5 to 32° C. as shown in FIG. 26. The linear heat balance equation derived was:

$$(T_{Location\ 2}-T_{faceplate})=3.039(T_{oral}-T_{Location\ 2})-0.9838 \quad (6)$$

Another experiment was run to test the newly available Murata high precision thermistors. The resulting heat balance equation (shown in FIG. 27) was:

$$(T_{Location\ 2}-T_{faceplate})=3.3766(T_{oral}-T_{Location\ 2})-0.1598 \quad (7)$$

Figure 27:
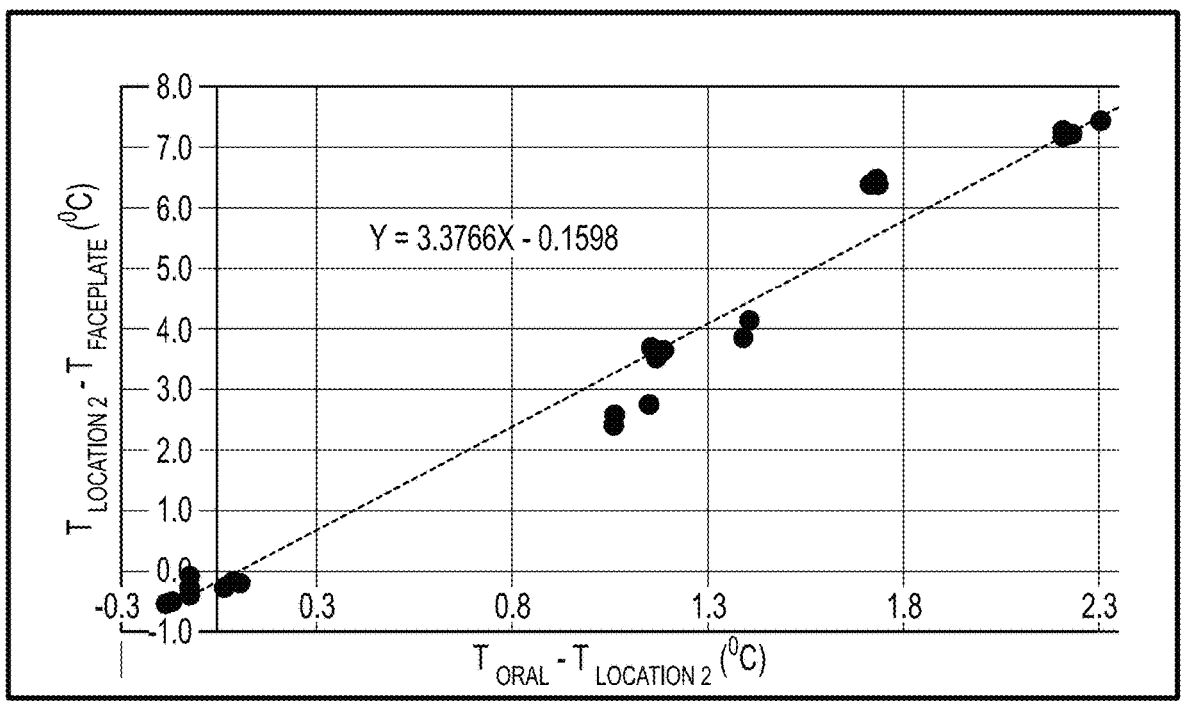
FIG. 27 is a graph illustrating a heat balance equation developed from three persons and derived from temperature measurements taken from a second type of temperature sensors in an ITE in accordance with various embodiments.
Figure 28:
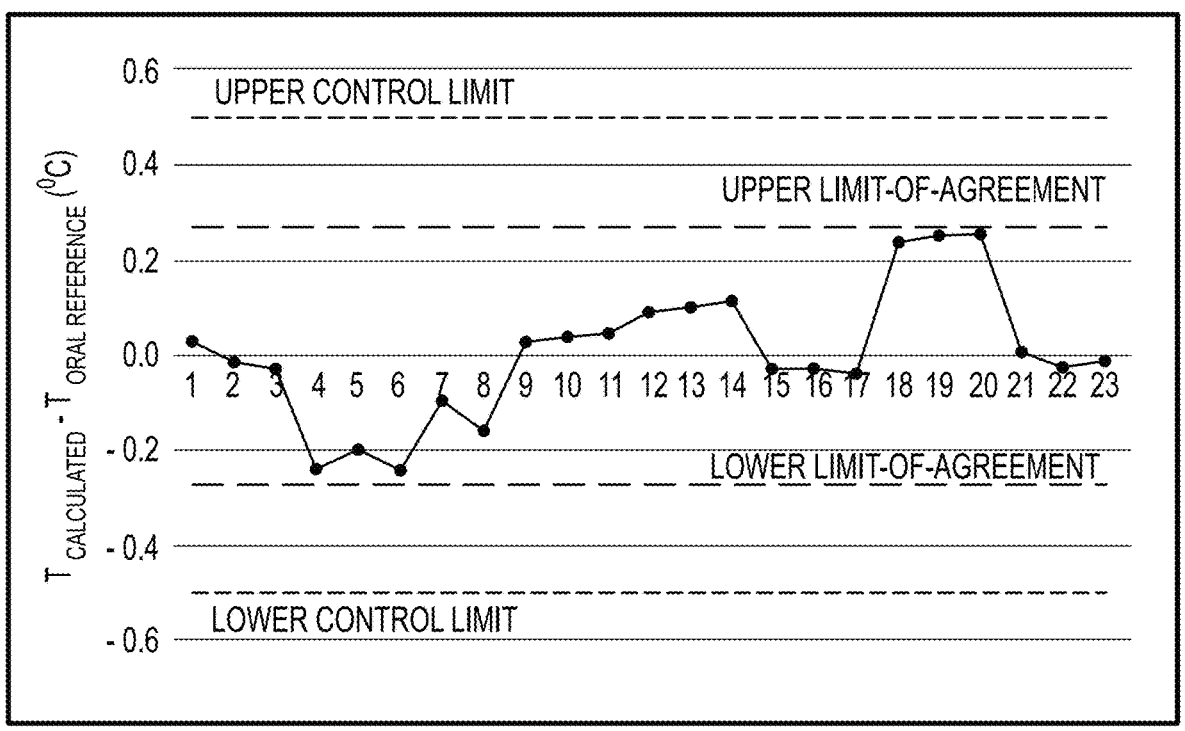
FIG. 28 is a graph showing the difference in core body temperature calculated from the heat balance equation of FIG. 27 in accordance with various embodiments.

FIG. 27 shows the resulting heat balance and FIG. 28 shows the results when the derived heat balance equation was applied to the data in order to calculate the core body temperature from the temperature obtained from the faceplate and Location 2 thermistors alone. All calculated core temperatures were well within +/−0.5° C. defined as acceptable to inform temperature as a health indicator and the limits-of-agreements (1.96σ) were calculated to be +/−0.27° C.

Subsequent experiments conducted over a range of environments including outdoors and wind conditions showed that the system was also capable of measuring accurate temperature beyond the typical indoor conditions.

Study 5. Modifying the Gradient Across the Ear Shell

The heat balance method using two thermistors to triangulate core body temperature can be used from any number of locations in the ear and any variety of ear device designs including an: AP-RIC (which has a custom ITE shell filled with silicone), ITC, CIC or IIC custom devices as well as any number of standard ear bud type hearing devices. These devices present significant materials and design challenges to obtain accurate temperature from within-a-person and from person-to-person due to environmental temperature changes as well draft.

Figure 29:
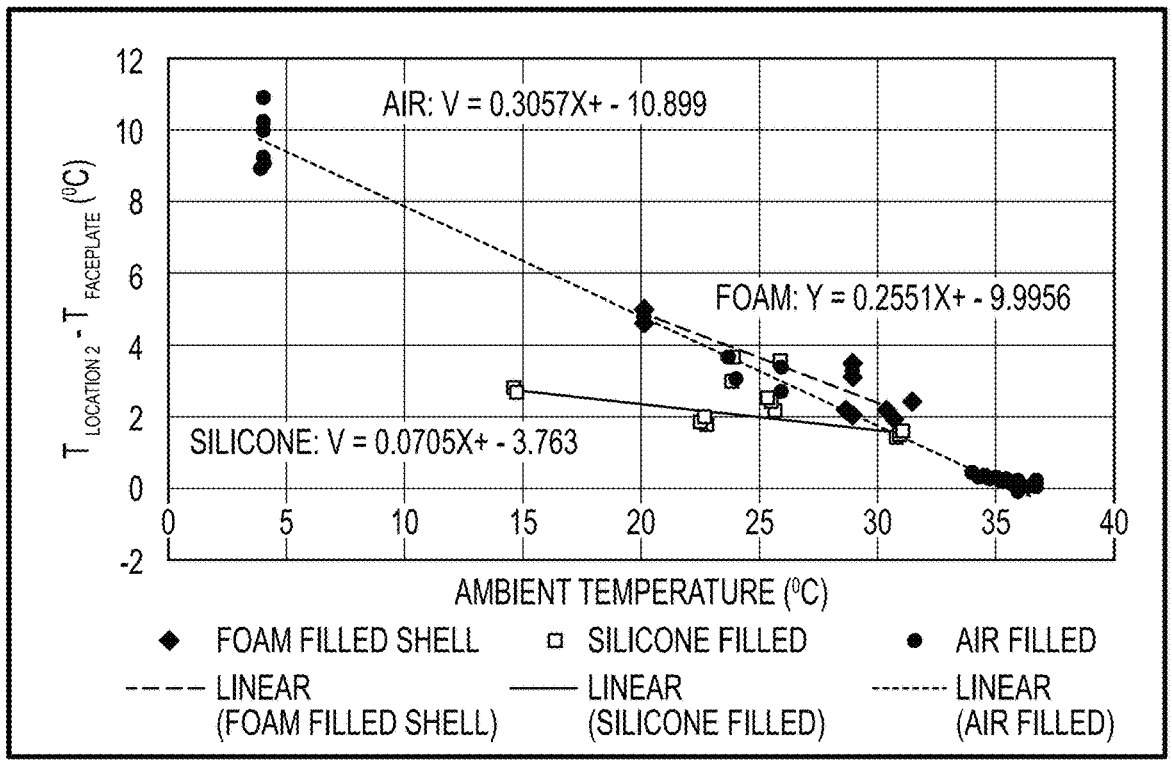
FIG. 29 shows a comparison of the heat balance for three materials systems in an ITE shell in accordance with various embodiments.

Materials can be added inside the shell, on the shell or under the shell to modify the temperature gradient across the ear device or to prevent adverse effects of environmental temperature or draft. And, materials can be designed to affect the radiative, convective or conductive heat transfer. FIG. 29 shows a comparison of the heat balance for three materials systems in an ITE shell with thermistors at Location 2 and the faceplate. FIG. 29 shows the results for the three fill materials (foam, silicone, air). All materials systems demonstrated a linear heat balance and resulted in accurate calculated temperature values when tested under 5 mph wind draft.

Figure 30:
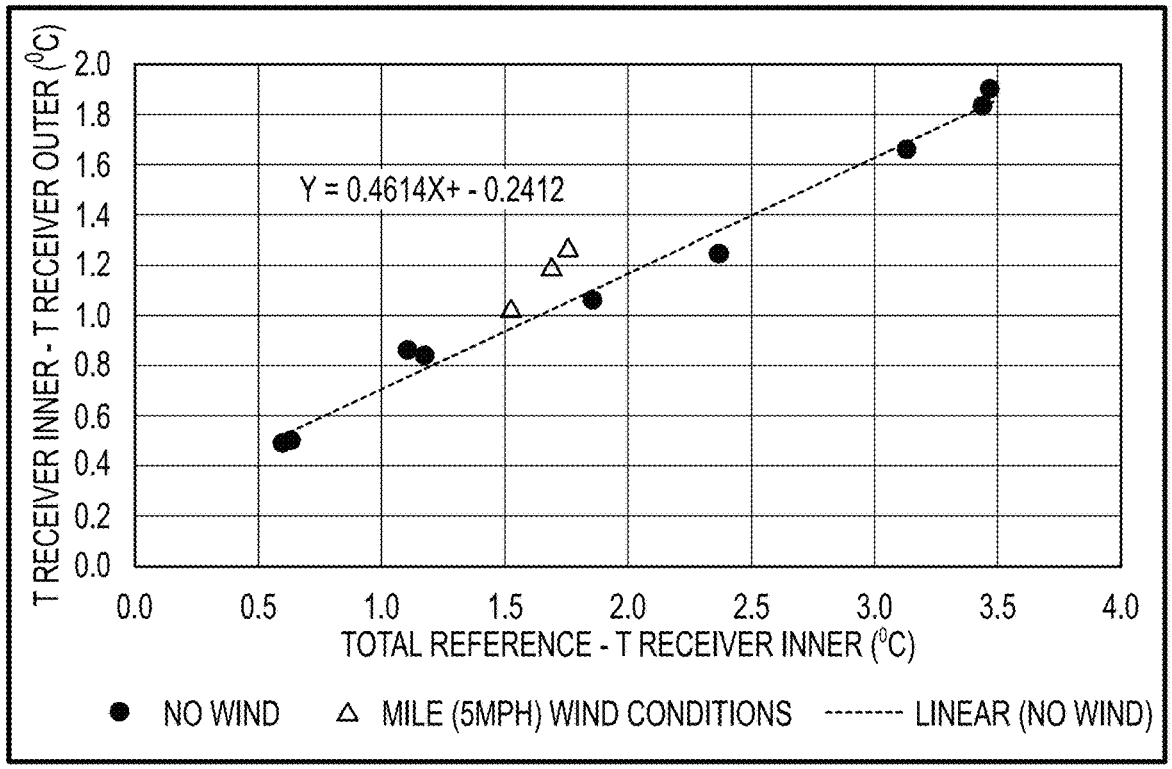
FIG. 30 shows a heat balance equation derived from two high precision temperature sensors on the receiver of a standard earbud hearing device and oral temperature from a reference probe in accordance with various embodiments.
Figure 31:
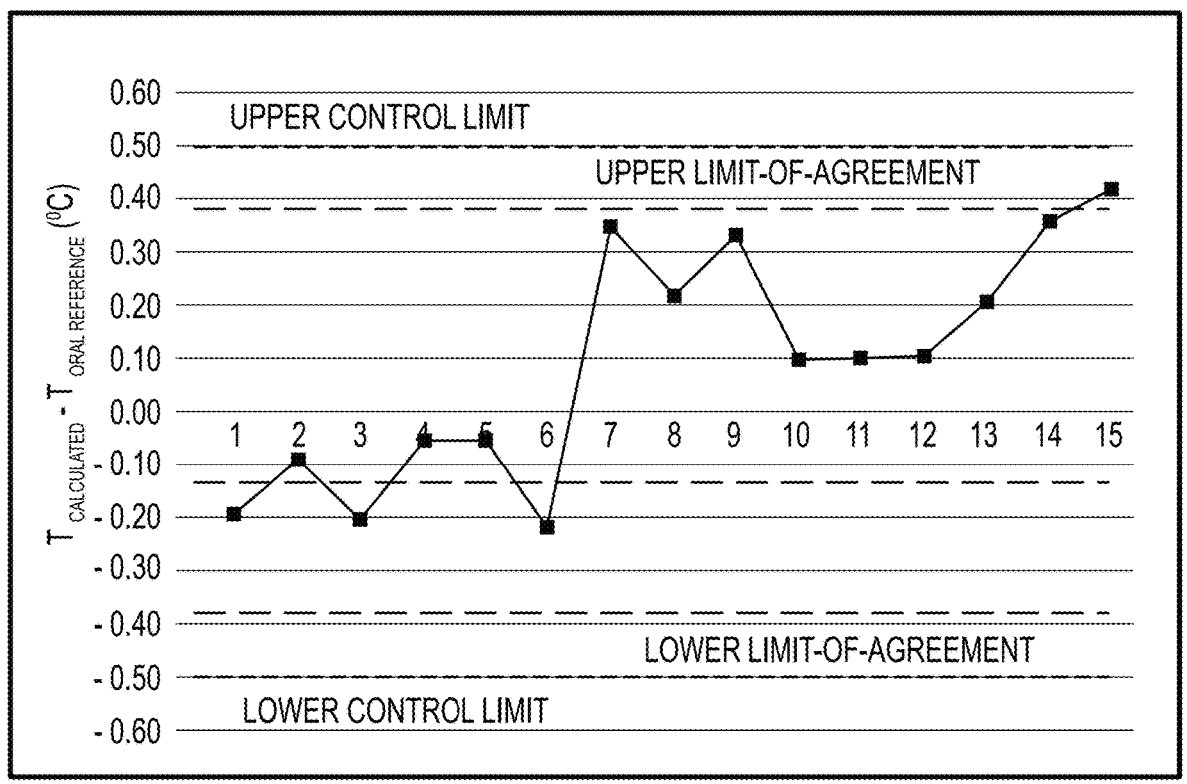
FIG. 31 shows the difference in core body temperature calculated from a heat balance equation derived from two high precision temperature sensors on the receiver of a standard earbud hearing device and oral temperature from a reference probe in accordance with various embodiments.

Study 6. Obtaining Accurate Body Temperature in a Range of Environmental Temperatures and Draft Using Thermistors Near the Receiver/Speaker of a Standard Earbud Hearing Device The concept of obtaining a heat balance from any two points in the ear was further explored in a standard hearing device that consists of a receiver with an earbud attached to it. The high precision Murata thermistors were placed on the side of the receiver at each end (interior and exterior with reference to the ear canal). FIG. 30 shows the heat balance equation resulting from one subject subjected to a temperature range of 14 to 30.5° C. with no wind. Three (3) additional tests were run in mild wind conditions. FIG. 31 shows the difference between the calculated core temperature and the temperature measured from the oral reference probe. The limits of agreement were found to be +/−0.29° C. without wind and +/−0.39° C. with wind. When this test sequence was repeated for 3 additional subjects, the heat balance equations were significantly different from person-to-person while the limits of agreement showed consistent precision.

Discussion

In an exploratory study, a non-invasive 2 thermistor temperature sensing system has been integrated into ear-worn hearing device designs. Temperature was measured at 2 thermistors placed along the temperature gradient of the ear over a range of environmental temperatures in order to derive a heat balance equation that was used to calculate core body temperature. The predicted core body temperatures resulted in limits of agreement (1.96σ) of +/−0.27° C. with 100% of the data within +/−0.5° C. for thermistors placed in an ITE hearing device. The limits of agreement included the person-to-person variability over a small sample size of normothermic persons without individual calibration of the biometric hearing device. The biometric hearing device system demonstrated the ability to accurately perform over a range of environmental temperatures and mild wind draft conditions which is essential for a continuously worn device.

Application of the 2 thermistor system to a standard earbud hearing device was explored. Limits of agreement (1.96σ) of +/−0.29° C. with 100% of the data within +/−0.5° C. were achieved for one person using thermistors mounted on the receiver and separated by air.

Double sensor systems in the past have used dual stacked thermistors with a material of known heat transfer coefficient in between them in order to predict core body temperature. The methods used in these systems resulted in much larger limits of agreement than the system developed in the ear. One study reported data equivalent to limits of agreements of +/−0.98, +/−0.73 and +/−0.82 in 10° C., 25° C. and 40° C. for a double sensor system integrated into the strap of a helmet and measuring temperature from the top of the head in comparison to a rectal thermometer. In another study, a double sensor placed on the forehead of preoperative patients reported limits of agreement of −0.66° C. to 0.50° C. when compared to an esophageal thermometer and 98% of values were within +/−0.5° C.

The differences in precision of these double sensor systems and the present system developed in the ear may be due to the location and interface of the devices to the body, the different use of a material or air in between the sensors and/or the empirical methods used to derive the core body temperature.

The method of using Bland-Altman plots to calculate limits of agreement was not useful for comparing body temperature measurement systems because the reference tool, the system under analysis and/or the ear changed with environmental temperature. This preempted the need to derive a heat balance relationship that factored out this variation to predict core body temperature.

The ability to empirically derive accurate heat balance relationships was also dependent on the accuracy and precision of the reference tool over the operational range studied. Studies of different less invasive thermometers have indicated that most are not precise to within +/−0.5° C. when compared to pulmonary or esophageal temperatures. The exception found was the clinical grade TAT5000 temporal thermometer, however it was not tested in wind conditions. The standard deviation for temperature measurements taken for the TAT5000 temporal thermometer was calculated as 0.2° C. while that calculated for an oral thermometer was 0.8° C. when compared to an esophageal thermometer. When infrared thermometry was compared to pulmonary artery temperatures in another study, there was a high degree of variability from subject to subject. Differences in oral and axillary temperatures had standard deviations of +/−0.6° C. and interactions with the environment were noted for both. While the data from the literature cannot be directly compared to those of 2 sensors systems, the ear-worn, 2 temperature sensor system of the present disclosure performs better than any of the other noninvasive systems.

The benefits of a continuously worn temperature measurement device are numerous. The thermistor system combined with a microprocessor, memory devices and clock function can capture the baseline circadian rhythm which varies as much as 0.5° C. or more over a 24-hour period. This information can be used to better predict increases or decreases in core temperature at a given time of day. Changes in mesor, amplitude and acrophase of the circadian cycle have been demonstrated to be altered in condition such as diabetes and early detection of these alterations may allow earlier intervention.

Continuous monitoring of temperature via a heat balance method can also detect subtle differences in the autonomic and endocrine thermoregulatory responses such as: 1) the onset of increased thermoregulatory control, 2) the overshoot in temperature during latency of the thermoregulatory response, 3) the onset of shivering or sweating and the resulting change in core temperature or skin temperature from those states. This has immense potential to illuminate the endocrine and autonomic functional state of the human in health, in diseases and in transitions between those states. The system can also provide primary information or secondary information to other biometrics such as heart rate, accelerometer, galvanic skin response and pulse oxygen in order to monitor the effect of daily living, food intake, substance exposure and pharmaceuticals on the human body. A communication device that provides quantitative data to individual users, providers of healthcare or caretakers is particularly important for those with conditions that prevent the device user from being aware of how the body is reacting or for persons who are unable to communicate their awareness to caretakers.

CONCLUSION

A novel system was developed in which the equilibrium (or heat balance) between the ear canal and an outer ear location was measured during varying environmental temperatures and draft in order to allow continuous accurate and precise prediction of absolute core body temperature measurements over a range of operational conditions. A heat balance method of calculating absolute core body temperatures from 2 thermistors in an in-the-ear custom hearing shell was demonstrated to result in limits of agreement with an oral reference probe of +/−0.27° C. over multiple people without individual calibration.

Hearing devices today have the capability of storing and transmitting data to external devices and provide an ideal communication tool for integration of biosensors. The ear is an ideal location for biosensors and hearing devices are continuously worn. The precise measurement capability of the ear-worn temperature measurement system developed in this exploratory study will allow: 1) discoveries in therapeutic treatments for conditions related to the autonomic and endocrine system such as diabetes and stress related disorders and 2) provide valuable information to users and caretakers to prevent continued states outside the thermoneutral zone either due to illness or environmental stressors.

Embodiments of temperature sensors and/or sensor systems described herein can be used to measure or predict a variety of different temperature measurements, changes and gradients. For example, various embodiments can be used to calculate or predict core body temperature, measure skin temperature, continuously measure the daily circadian rhythm of core body temperature or skin temperature and establish an individual's "baseline" temperature for a given time of day or over the course of the entire day. Embodiments can be used to calculate the mesor, amplitude, and acrophase of the daily circadian rhythm using cosinor analysis, determine the magnitude of the change in core body or skin temperature over any period of time, and measure increases and decreases in core body or skin temperature relative to a baseline. The baseline may be computed as an average (mean, median or mode) or a moving average of the temperature over one or more pre-determined periods of time, including the entire duration of device usage up to the time instant of the computation.

Embodiments can be used to measure the time of onset of the response to a change that effect the thermoregulatory rate, measure the time of occurrence for sweating, the decrease in temperature from peak temperature due to sweating and the increase in temperature from baseline under sweating conditions. Embodiments can be used to measure the time of occurrence for shivering, the increase in temperature from maximum low temperature due to shivering, and the final net decrease in temperature from baseline under shivering conditions. Embodiments can be used to measure the minimum and maximum threshold boundary temperatures of the thermo-neutral zone and the time of occurrence and identify temperatures outside that zone.

Embodiments can be used to measure temperature and time of onset of a physiological change due to a change in environmental temperature or draft, hot/cold water immersion, vasodilation/vasoconstriction, sweating, and shivering. Embodiments can be used to measure temperature and time of onset of a physiological change due to response to drugs or other chemicals that illicit an autonomic or endocrine response in the form of a skin or core body temperature change, physiological response due to stress or other emotions, physical activity, and a pre-determined amount of heart rate change. Embodiments can be used to measure the difference in temperature or time of occurrence for any of the above.

Embodiments can be used to differentiate between responses due to exogenous (environmental) versus endogenous (physiological) changes in order to provide primary health information or to act as a second sensor system to prevent false positive or false negative indicators from one or more other sensors, measure the frequency of the combined thermoregulatory response at the ear, and/or predict caloric expenditure, amongst others.

According to various embodiments, temperature data can be collected using a variety of techniques. For example, techniques could include measuring resistance of two or more thermistors within the ear. Resistance can be converted to temperature using a lookup table based on the Steinhart-Hart equation. A linear algorithm can be used to calculate an actual core body temperature. A linear algorithm can be used to calculate an actual environmental temperature. A linear algorithm can be used to calculate an actual wind speed body temperature. A neural network or SVM (support vector machine) algorithm can be used to calculate the core and environmental temperatures and wind speed.

Embodiments can be used to store a cumulative moving average, or exponential moving average of core temperature with varying window sizes (1 hr, 1 day, 1 week, 1 month, 1 year). Average data can be used to detect temperate anomalies indicating different health states. Calculated and/or measured temperature can be stored in internal memory. Calculated and/or measured temperature can be communicated out of the ear device over a wireless connection (e.g., Bluetooth®, Bluetooth® Low Energy (BLE), WiFi, or other IEEE 802.11 compliant interface) to a device with more processing power (e.g., phone, accessory, computer, cloud). Complex algorithms can be used to determine health state (e.g., fever, hypothermia, etc.). Additional sensor data and complex algorithms can be used to determine health status (e.g., blood pressure, glucose, athletic performance, etc.). Resistance data can be stored in internal memory of the ear device (to be sent to a device with more memory and processing power later).

According to some embodiments, resistance data can be communicated from an ear device to a device with more memory and processing power. Such a device can use an algorithm to calculate an actual core body temperature, an algorithm to calculate an actual environmental temperature, and/or an algorithm to calculate an actual wind speed body temperature. Such a device can use a neural network or SVM algorithm to calculate core temperature, environmental temperature, and wind speed. Such a device can use algorithms to determine health state (e.g., fever, hypothermia, etc.), and use additional sensor data and algorithms to determine health status (e.g., blood pressure, glucose, athletic performance, etc.). Such a device can store a cumulative moving average or exponential moving average of core temperature with varying window sizes (1 hr, 1 day, 1 week, 1 month, 1 year), and use average data to detect temperate anomalies indicating different health states. Such a device can be configured to capture fast resistance data (>10 Hz) (no need to convert to an actual temperature), use data to detect fast changing biological signals (e.g., heart rate), and use data with other sensors to detect fast changing biological signals (e.g., blood pressure, glucose, stress, etc.).

This document discloses numerous embodiments, including but not limited to the following:

Item 1 is an ear-worn electronic device configured to measure temperature from within an ear canal of an ear comprising a first bend and a second bend, the device comprising:
an enclosure configured for insertion into the ear canal and comprising a distal end configured to extend at least beyond the first bend;
a distal temperature sensor situated at a location of the enclosure that faces a tragus-side of the ear canal distal to the first bend and proximal to the second bend when the enclosure is fully inserted into the ear canal, the distal temperature sensor configured to sense one or both of conductive heat and convective heat and to produce a first temperature signal;
a proximal temperature sensor situated on the enclosure at a location spaced apart from a surface of the ear canal and proximal of the distal temperature sensor in an outer ear direction when the enclosure is fully inserted into the ear canal, the proximal temperature sensor configured to sense one or both of conductive heat and convective heat and to produce a second temperature signal;
a memory configured to store a pre-established heat balance equation; and
a processor coupled to the distal and proximal temperature sensors and to the memory, the processor configured to calculate an absolute core body temperature using the heat balance equation and the first and second temperature signals.

Item 2 is the device of item 1, wherein the distal temperature sensor is situated at the location of the enclosure that faces a superficial temporal artery branch of the external carotid artery when the enclosure is fully inserted into the ear canal.

Item 3 is the device of item 1, wherein:
a temperature measured by the distal temperature sensor is closer to the body core temperature than a temperature measured by the proximal temperature sensor; and
the temperature measured by the proximal temperature sensor is closer to an ambient temperature than the temperature measured by the distal temperature sensor.

Item 4 is the device of item 1, wherein the pre-established heat balance equation characterizes a temperature gradient of the ear for a population of persons over a range of ambient temperatures.

Item 5 is the device of item 1, wherein the absolute core body temperature calculated by the processor has an error within +/−0.5° C. relative to a reference core body temperature over one or both of a range of ambient temperatures and a range of wind draft conditions.

Item 6 is the device of item 1, wherein the distal temperature sensor is situated on the enclosure to establish contact with ear canal tissue at the tragus-side of the ear canal.

Item 7 is the device of item 1, wherein the distal temperature sensor is recessed into, or situated within, the enclosure and thermally coupled to ear canal tissue at the tragus-side of the ear canal.

Item 8 is the device of item 1, wherein at least a portion of the distal temperature sensor facing the tragus-side of the ear canal is covered with a thermally conductive material.

Item 9 is the device of item 1, wherein at least a portion of the distal temperature sensor in contact with or penetrating into the enclosure is surrounded by thermally insulating material.

Item 10 is an ear-worn hearable comprising the device of item 1.

Item 11 is a hearing aid comprising the device of item 1.

Item 12 is a diagnostic instrument comprising the device of item 1, wherein the diagnostic instrument comprises:
a hand-graspable handle section;
an instrument head coupled to the handle section and comprising at least the distal temperature sensor;
a display configured to display at least the absolute body core temperature; and
a power source.

Item 13 is a method implemented by an electronic device configured for insertion into an ear canal of an ear, the ear canal comprising a first bend, a second bend, and a tragus-side, the method comprising:
measuring a first temperature indicative of one or both of conductive heat and convective heat at the tragus-side of the ear canal between the first and second bends;
measuring a second temperature indicative of one or both of conductive heat and convective heat at a location spaced apart from a surface of the ear canal and proximal of an ear canal location where the first temperature is measured in an outer ear direction;
storing, in a memory of the device, a pre-established heat balance equation; and
calculating, using a processor of the device, an absolute core body temperature using the heat balance equation and the first and second temperatures.

Item 14 is the method of item 13, wherein the first temperature is representative of a temperature of blood supplied to a superficial temporal artery branch of the external carotid artery.

Item 15 is the method of item 13, wherein:
the first temperature is closer to the body core temperature than the second temperature; and
the second temperature is closer to an ambient temperature than the first temperature.

Item 16 is the method of item 13, wherein the pre-established heat balance equation characterizes a temperature gradient of the ear for a population of persons over a range of ambient temperatures.

Item 17 is the method of item 13, wherein the absolute core body temperature calculated by the processor has an error within +/−0.5° C. relative to a reference core body temperature over one or both of a range of ambient temperatures and a range of wind draft conditions.

Item 18 is the method of item 13 implemented by an ear-worn hearable comprising the electronic device.

Item 19 is the method of item 13 implemented by a hearing aid comprising the electronic device.

Item 20 is the method of item 13 implemented by a hand-held diagnostic instrument comprising the electronic device, the method further comprising displaying at least the absolute body core temperature on a display of the diagnostic instrument.

Item 21 is an ear-worn electronic device configured to be worn in an ear of a wearer and to measure temperature from within an ear canal of the ear comprising a first bend and a second bend, the device comprising:
an enclosure configured for insertion into the ear canal and comprising a distal end configured to extend at least beyond the first bend;

a distal temperature sensor situated at a location of the enclosure that faces a tragus-side of the ear canal distal to the first bend and proximal to the second bend when the enclosure is fully inserted into the ear canal, the distal temperature sensor configured to sense one or both of conductive heat and convective heat and to produce a first temperature signal;

a proximal temperature sensor situated on the enclosure at a location in the ear that is spaced apart from a surface of the ear canal and proximal of the distal temperature sensor in an outer ear direction when the enclosure is fully inserted into the ear canal, the proximal temperature sensor configured to sense one or both of conductive heat and convective heat and to produce a second temperature signal;

a memory configured to store a pre-established heat balance equation; and a processor coupled to the distal and proximal temperature sensors and to the memory, the processor configured to calculate an absolute core body temperature using the heat balance equation and the first and second temperature signals.

Item 22 is the device of item 21, wherein the ear-worn electronic device is configured as an in-the-ear (ITE) device, an in-the-canal (ITC) device, a completely-in-canal (CIC) device or an invisible-in-the-canal (IIC) device.

Although reference is made herein to the accompanying set of drawings that form part of this disclosure, one of at least ordinary skill in the art will appreciate that various adaptations and modifications of the embodiments described herein are within, or do not depart from, the scope of this disclosure. For example, aspects of the embodiments described herein may be combined in a variety of ways with each other. Therefore, it is to be understood that, within the scope of the appended claims, the claimed invention may be practiced other than as explicitly described herein.

All references and publications cited herein are expressly incorporated herein by reference in their entirety into this disclosure, except to the extent they may directly contradict this disclosure. Unless otherwise indicated, all numbers expressing feature sizes, amounts, and physical properties used in the specification and claims may be understood as being modified either by the term "exactly" or "about." Accordingly, unless indicated to the contrary, the numerical parameters set forth in the foregoing specification and attached claims are approximations that can vary depending upon the desired properties sought to be obtained by those skilled in the art utilizing the teachings disclosed herein or, for example, within typical ranges of experimental error.

The recitation of numerical ranges by endpoints includes all numbers subsumed within that range (e.g. 1 to 5 includes 1, 1.5, 2, 2.75, 3, 3.80, 4, and 5) and any range within that range. Herein, the terms "up to" or "no greater than" a number (e.g., up to 50) includes the number (e.g., 50), and the term "no less than" a number (e.g., no less than 5) includes the number (e.g., 5).

The terms "coupled" or "connected" refer to elements being attached to each other either directly (in direct contact with each other) or indirectly (having one or more elements between and attaching the two elements). Either term may be modified by "operatively" and "operably," which may be used interchangeably, to describe that the coupling or connection is configured to allow the components to interact to carry out at least some functionality (for example, a radio chip may be operably coupled to an antenna element to provide a radio frequency electric signal for wireless communication).

Terms related to orientation, such as "top," "bottom," "side," and "end," are used to describe relative positions of components and are not meant to limit the orientation of the embodiments contemplated. For example, an embodiment described as having a "top" and "bottom" also encompasses embodiments thereof rotated in various directions unless the content clearly dictates otherwise.

Reference to "one embodiment," "an embodiment," "certain embodiments," or "some embodiments," etc., means that a particular feature, configuration, composition, or characteristic described in connection with the embodiment is included in at least one embodiment of the disclosure. Thus, the appearances of such phrases in various places throughout are not necessarily referring to the same embodiment of the disclosure. Furthermore, the particular features, configurations, compositions, or characteristics may be combined in any suitable manner in one or more embodiments.

The words "preferred" and "preferably" refer to embodiments of the disclosure that may afford certain benefits, under certain circumstances. However, other embodiments may also be preferred, under the same or other circumstances. Furthermore, the recitation of one or more preferred embodiments does not imply that other embodiments are not useful and is not intended to exclude other embodiments from the scope of the disclosure.

As used in this specification and the appended claims, the singular forms "a," "an," and "the" encompass embodiments having plural referents, unless the content clearly dictates otherwise. As used in this specification and the appended claims, the term "or" is generally employed in its sense including "and/or" unless the content clearly dictates otherwise. As used herein, "have," "having," "include," "including," "comprise," "comprising" or the like are used in their open-ended sense, and generally mean "including, but not limited to." It will be understood that "consisting essentially of," "consisting of," and the like are subsumed in "comprising," and the like. The term "and/or" means one or all of the listed elements or a combination of at least two of the listed elements.

The phrases "at least one of," "comprises at least one of," and "one or more of" followed by a list refers to any one of the items in the list and any combination of two or more items in the list.

What is claimed is:

1. An electronic device configured to measure temperature from within an ear canal of an ear comprising a first bend and a second bend, the device comprising:

an enclosure configured for insertion into the ear canal and comprising a distal end configured to extend at least beyond the first bend;

a distal temperature sensor situated at a location of the enclosure that faces a tragus-side of the ear canal distal to the first bend and proximal to the second bend when the enclosure is fully inserted into the ear canal, the distal temperature sensor configured to sense one or both of conductive heat and convective heat and to produce a first temperature signal;

a proximal temperature sensor situated on the enclosure at a location spaced apart from a surface of the ear canal and proximal to the distal temperature sensor location in an outer ear direction when the enclosure is fully inserted into the ear canal, the proximal temperature sensor configured to sense one or both of conductive heat and convective heat and to produce a second temperature signal;

a memory configured to store a pre-established heat balance equation; and a processor coupled to the distal and proximal temperature sensors and the memory, the processor configured to calculate an absolute core body temperature using the heat balance equation and the first and second temperature signals.

2. The device of claim 1, wherein the distal temperature sensor is situated at a location of the enclosure that faces a superficial temporal artery branch of an external carotid artery when the enclosure is fully inserted into the ear canal.

3. The device of claim 1, wherein:
a temperature measured by the distal temperature sensor is closer to a body core temperature than a temperature measured by the proximal temperature sensor; and
the temperature measured by the proximal temperature sensor is closer to an ambient temperature than the temperature measured by the distal temperature sensor.

4. The device of claim 1, wherein the pre-established heat balance equation characterizes a temperature gradient of the ear for a population of persons over a range of ambient temperatures.

5. The device of claim 1, wherein the absolute core body temperature calculated by the processor has an error within +/−0.5° C. relative to a reference core body temperature over one or both of a range of ambient temperatures and a range of wind draft conditions.

6. The device of claim 1, wherein the distal temperature sensor is situated on the enclosure to establish contact with ear canal tissue at the tragus-side of the ear canal.

7. The device of claim 1, wherein the distal temperature sensor is recessed into, or situated within, the enclosure and thermally coupled to ear canal tissue at the tragus-side of the ear canal.

8. The device of claim 1, wherein at least a portion of the distal temperature sensor facing the tragus-side of the ear canal is covered with a thermally conductive material.

9. The device of claim 1, wherein at least a portion of the distal temperature sensor in contact with or penetrating into the enclosure is surrounded by thermally insulating material.

10. An ear-worn hearable comprising the device of claim 1.

11. A hearing aid comprising the device of claim 1.

12. A diagnostic instrument comprising the device of claim 1, wherein the diagnostic instrument comprises:
a hand-graspable handle section;
an instrument head coupled to the handle section and comprising at least the distal temperature sensor;
a display configured to display at least the absolute body core temperature; and
a power source.

13. The device of claim 1, wherein the distal temperature sensor is situated within the enclosure and configured to thermally couple to ear canal tissue at the tragus-side of the ear canal.

14. A method implemented by an electronic device configured for insertion into an ear canal of an ear, the ear canal comprising a first bend, a second bend, and a tragus-side, the method comprising:
measuring a first temperature indicative of one or both of conductive heat and convective heat at the tragus-side of the ear canal between the first and second bends;
measuring a second temperature indicative of one or both of conductive heat and convective heat at a location spaced apart from a surface of the ear canal and proximal of an ear canal location where the first temperature is measured in an outer ear direction;
storing, in a memory of the device, a pre-established heat balance equation; and
calculating, using a processor of the device, an absolute core body temperature using the heat balance equation and the first and second temperatures.

15. The method of claim 14, wherein the first temperature is representative of a temperature of blood supplied to a superficial temporal artery branch of the external carotid artery.

16. The method of claim 14, wherein:
the first temperature is closer to a body core temperature than the second temperature; and
the second temperature is closer to an ambient temperature than the first temperature.

17. The method of claim 14, wherein the pre-established heat balance equation characterizes a temperature gradient of the ear for a population of persons over a range of ambient temperatures.

18. The method of claim 14, wherein the absolute core body temperature calculated by the processor has an error within +/−0.5° C. relative to a reference core body temperature over one or both of a range of ambient temperatures and a range of wind draft conditions.

19. The method of claim 14 implemented by an ear-worn hearable comprising the electronic device.

20. The method of claim 14 implemented by a hearing aid comprising the electronic device.

21. The method of claim 14 implemented by a hand-held diagnostic instrument comprising the electronic device, the method further comprising displaying at least the absolute body core temperature on a display of the diagnostic instrument.

22. An ear-worn electronic device configured to be worn in an ear of a wearer and to measure temperature from within an ear canal of the ear comprising a first bend and a second bend, the device comprising:
an enclosure configured for insertion into the ear canal and comprising a distal end configured to extend at least beyond the first bend;
a distal temperature sensor situated at a location of the enclosure that faces a tragus-side of the ear canal distal to the first bend and proximal to the second bend when the enclosure is fully inserted into the ear canal, the distal temperature sensor configured to sense one or both of conductive heat and convective heat and to produce a first temperature signal;
a proximal temperature sensor situated on the enclosure at a location in the ear that is spaced apart from a surface of the ear canal and proximal of the distal temperature sensor in an outer ear direction when the enclosure is fully inserted into the ear canal, the proximal temperature sensor configured to sense one or both of conductive heat and convective heat and to produce a second temperature signal;
a memory configured to store a pre-established heat balance equation; and
a processor coupled to the distal and proximal temperature sensors and to the memory, the processor configured to calculate an absolute core body temperature using the heat balance equation and the first and second temperature signals.

23. The device of claim 22, wherein the ear-worn electronic device is configured as an in-the-ear (ITE) device, an in-the-canal (ITC) device, a completely-in-canal (CIC) device or an invisible-in-the-canal (IIC) device.

* * * * *